US011021488B2

(12) United States Patent
Guzman et al.

(10) Patent No.: US 11,021,488 B2
(45) Date of Patent: Jun. 1, 2021

(54) HETERO-SUBSTITUTED CYCLIC LACTONE ANALOGUES AND USES THEREOF

(71) Applicants: BioVentures, LLC, Little Rock, AR (US); Cornell University, Ithaca, NY (US); New York Botanical Garden, Bronx, NY (US)

(72) Inventors: Monica L. Guzman, Ithaca, NY (US); Cesar M. Compadre, Little Rock, AR (US); Paola E. Ordonez, Little Rock, AR (US); Mariano Martinez, Little Rock, AR (US); Michael J. Balick, Bronx, NY (US); Darin E. Jones, Little Rock, AR (US); Flavio G. Gaudio, Ithaca, NY (US)

(73) Assignees: Board of Trustees of the University of Arkansas, Little Rock, AR (US); BioVentures, LLC, Little Rock, AR (US); Cornell University, Ithaca, NY (US); New York Botanical Garden, Bronx, NY (US)

( * ) Notice: Subject to any disclaimer, the term of this patent is extended or adjusted under 35 U.S.C. 154(b) by 0 days.

(21) Appl. No.: 16/523,687

(22) Filed: Jul. 26, 2019

(65) Prior Publication Data
US 2019/0345167 A1 Nov. 14, 2019

Related U.S. Application Data

(63) Continuation of application No. 15/773,902, filed as application No. PCT/US2016/060318 on Nov. 3, 2016, now abandoned.

(60) Provisional application No. 62/251,463, filed on Nov. 5, 2015.

(51) Int. Cl.
| C07D 493/10 | (2006.01) |
| C07D 307/93 | (2006.01) |
| C07D 493/04 | (2006.01) |
| C07D 493/18 | (2006.01) |
| C07D 493/08 | (2006.01) |

(52) U.S. Cl.
CPC ......... C07D 493/10 (2013.01); C07D 307/93 (2013.01); C07D 493/04 (2013.01); C07D 493/08 (2013.01); C07D 493/18 (2013.01)

(58) Field of Classification Search
None
See application file for complete search history.

(56) References Cited

U.S. PATENT DOCUMENTS

| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |

FOREIGN PATENT DOCUMENTS

WO  2017079429 A1  5/2017

OTHER PUBLICATIONS

Zhang, Q. et al., J. Med. Chem. 2012 vol. 55, pp. 8757-8769.*
Kupchan, S. M. et al., J. Org. Chem. 1969 vol. 34 pp. 3876-3883.*
Romo de Vivar Can. J. Chem 1969 vol. 47 pp. 2849-52.*
International Search Report and Written Opinion dated Feb. 6, 2017 from related International Patent Application No. PCT/US2016/060318; 10 pgs.
Office Action dated Jan. 28, 2019 from related U.S. Appl. No. 15/773,902; 5 pgs.
PubChem Compound Summary for CID 24897814, Created Sep. 22, 2008, Modified Dec. 24, 2016; 8 pgs.
Tori, M. et al., "Sesquiterpenoids Isolated from Eupatorium glehnii. Isolation of Guaiaglehnin A, Structure Revision of Hiyodorilactone B, and Genetic Comparison," Chem. Pharm. Bull., May 2008, pp. 677-681, vol. 56, No. 5, Pharmaceutical Society of Japan.
Zhang, Q. et al., "Guaianolide Sesquiterpene Lactones, a Source to Discover Agents That Selectively Inhibit Acute Myelogenous Leukemia Stem and Progenitor Cells," J. Med. Chem., 2012, pp. 8757-8769, vol. 55.
CAPLUS Accession No. 1972:83505.
Herz, W. et al., "Glycosidic Disecoeudesmanolides and Other Secosesquiterpene Lactones from Picradeniopsis Species. X-ray Analysis of Bahia I," J. Org. Chem., 1980, pp. 3163-3172, vol. 45, No. 16.
Romo de Vivar, A. et al., "Structures of bahia-I and bahia-II: two new guaianolides," Can. J. Chem., 1969, pp. 2849-2852, vol. 47.
Cheng, Computation of Octanol-Water Partition Coefficients by Guilding an Additive Model with Knowledge, J. Chem. Inf. Model., 2007, pp. 2140-2148, vol. 47.

* cited by examiner

*Primary Examiner* — Heidi Reese
(74) *Attorney, Agent, or Firm* — Polsinelli PC

(57) ABSTRACT

The present disclosure provides SL and SL derivatives comprising a polar substituent adjacent to the lactone ring. Additionally, the present disclosure provides methods of using the SL and SL derivatives to inhibit the growth of leukemic cancer cells.

13 Claims, 18 Drawing Sheets
(17 of 18 Drawing Sheet(s) Filed in Color)

Calaxin
LD$_{50}$ = 0.0544 µM

PTL
LD$_{50}$ = 2.39 µM

DHL
$LD_{50} = 3.19\ \mu M$

Glaucolide A
$LD_{50}$ = 1.82 μM

Glaucolide E
$LD_{50}$ = 1.12 μM

Lipophilic area of the NF-κβ active site corresponding to Tyr-36 and Cys-38

HETERO-SUBSTITUTED CYCLIC LACTONE ANALOGUES AND USES THEREOF

CROSS REFERENCE TO RELATED APPLICATIONS

This application claims the benefit of U.S. patent application Ser. No. 15/773,902, filed May 4, 2018, which claims the benefit of International Patent Application number PCT/US2016/060318, filed Nov. 3, 2016, which claims the benefit of U.S. Provisional Application No. 62/251,463, filed Nov. 5, 2015, the disclosures of which are hereby incorporated by reference in their entirety.

GOVERNMENTAL RIGHTS

This invention was made with government support under DP2 OD007399-01 awarded by the National Institutes of Health. The government has certain rights in the invention.

FIELD OF THE INVENTION

The present disclosure relates to the use of sesquiterpene lactones (SLs) and to the use of SL derivatives for the treatment of various types of leukemic cancers including: acute lymphoblastic leukemia, chronic lymphocytic leukemia, acute myelogenous leukemia, chronic myeloid leukemia, and cutaneous T cell leukemia (CTCL).

BACKGROUND OF THE INVENTION

Many species of higher plants are used for healthcare purposes and a large number of the current anticancer drugs originate from natural sources. Given the wide variety of biologically active natural compounds and their wide structural diversity, it may be worthwhile to continue screening plants for compounds that could be useful as chemotherapeutic agents. Sesquiterpene lactones constitute a large and diverse group of biologically active plant chemicals that have been identified in several plant families. Some sesquiterpene lactones possess anti-inflammatory and/or antitumor activity. For example, parthenolide is highly cytotoxic, and a derivative of parthenolide is being tested in clinical trials as an anticancer agent. Parthenolide, however, has poor solubility and bioavailability, thus limiting its clinical use. There is a need, therefore, for new water-soluble compounds with robust cytotoxic anticancer properties.

SUMMARY OF THE INVENTION

In an aspect, the disclosure provides a compound comprising Formula (I) or a pharmaceutically acceptable salt thereof:

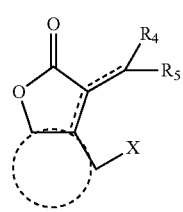

(I)

wherein:
X is a polar substituent;
$R_4$ and $R_5$ are independently selected from the group consisting of hydrogen, hydrocarbyl and substituted hydrocarbyl;
------ is a single or double bond; and
◌ a SL ring structure, minus the lactone ring, from the class of SLs including germacranolides, heliangolides, guaianolides, pseudoguaianolides, hypocretenolides, and eudesmanolides.

In another aspect, the disclosure provides a compound comprising Formula (Ia) or a pharmaceutically acceptable salt thereof:

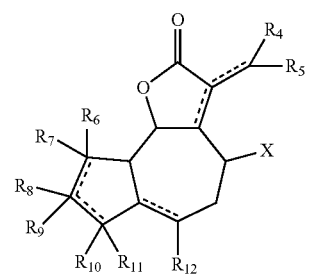

(Ia)

wherein:
X is a polar substituent;
$R_4$ and $R_5$ are independently selected from the group consisting of hydrogen, hydrocarbyl and substituted hydrocarbyl;
------ is a single or double bond; and
$R_6$, $R_7$, $R_8$, $R_9$, $R_{10}$, $R_{11}$ and $R_{12}$ are independently selected from the group consisting of hydrogen, hydrocarbyl and substituted hydrocarbyl.

In still another aspect, the disclosure provides a compound comprising Formula (II) or a pharmaceutically acceptable salt thereof:

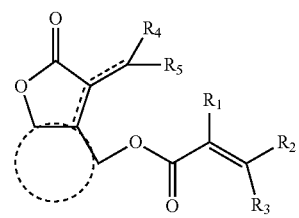

(II)

wherein:
$R_1$, $R_2$ and $R_3$ are independently selected from the group consisting of hydrogen, hydrocarbyl and substituted hydrocarbyl;
$R_4$ and $R_5$ are independently selected from the group consisting of hydrogen, hydrocarbyl and substituted hydrocarbyl;
------ is a single or double bond; and
◌ is a SL ring structure, minus the lactone ring, from the class of SLs including germacranolides, heliangolides, guaianolides, pseudoguaianolides, hypocretenolides, and eudesmanolides.

In still yet another aspect, the disclosure provides a method for inhibiting growth of a cancer cell derived from a blood cancer, the method comprising contacting the cancer cell with an effective amount of a composition comprising a SL or SL derivative, wherein the SL or SL derivative comprises a polar substituent adjacent to the lactone ring.

BRIEF DESCRIPTION OF THE DRAWINGS

The application file contains at least one drawing executed in color. Copies of this patent application publication with color drawing(s) will be provided by the Office upon request and payment of the necessary fee.

FIG. 13A depicts a graph showing a significant reduction in radiance emitted from tumor cells following administration of Bahia II. FIG. 13B depicts images of the whole animal showing the reduction in radiance following treatment with Bahia II.

DETAILED DESCRIPTION OF THE INVENTION

Figure 1A:
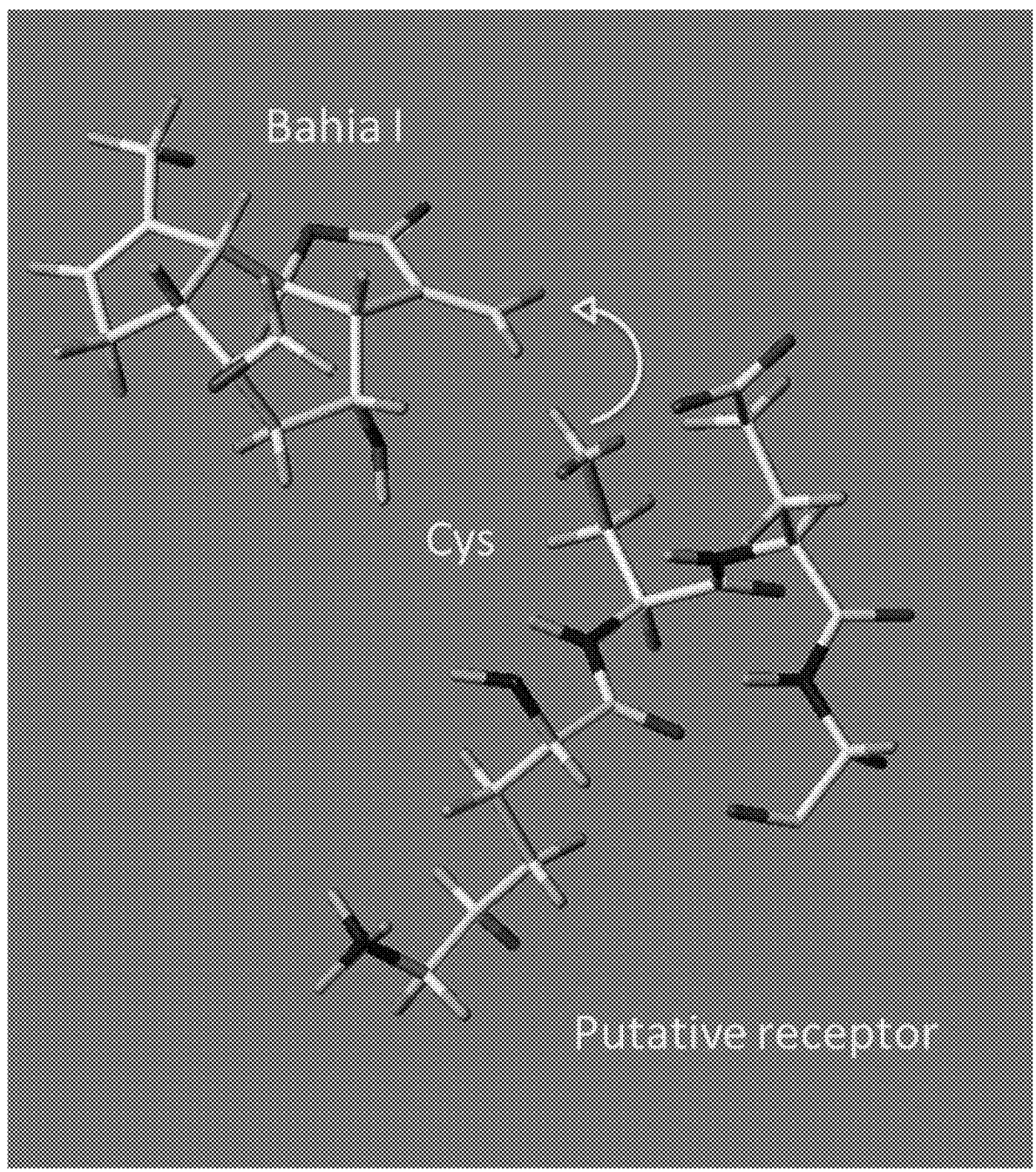
FIG. 1A depicts the mechanism of action of SLs. SLs react by a nucleophilic addition mechanism with the Cys-38 residue in the p65 subunit of NF-κB, preventing it from binding to DNA.

Applicants have discovered that sesquiterpene lactones (SLs), as well as derivatives thereof, selectively kill leukemic cancer cells. Accordingly, provided herein are compositions comprising SLs and derivatives of SLs. Primary among the various SLs derivatives is the presence of a polar substituent adjacent to the lactone ring and, optionally, an α-methylene group of the γ-lactone ring. In certain embodiments, the polar substituent is a methacrylate ester side chain. The disclosed SLs have improved water solubility relative to dehydroleucodine. Importantly, the α-methylene group of the γ-lactone ring and/or the polar substituent adjacent to the lactone ring react with NF-κB thereby preventing NF-κB from binding to DNA. In certain embodiments, the methacrylate ester side chain adjacent to the lactone ring reacts with NF-κB thereby preventing NF-κB from binding to DNA. Also provided herein are methods of using SLs or derivatives of SLs to inhibit the growth, proliferation, and metastasis of leukemic cancer cells. SLs or derivatives of SLs, therefore, may be used to treat leukemias.

I. Compositions

In an aspect, a composition of the disclosure comprises a SL or a SL derivative. A SL or SL derivative may be modified to improve potency, bioavailability, solubility, stability, handling properties, or a combination thereof, as compared to an unmodified version. Thus, in another aspect, a composition of the disclosure comprises a modified SL or SL derivative. In still another aspect, a composition of the disclosure comprises a prodrug of a SL or SL derivative.

A composition of the disclosure may optionally further comprise one or more SL or SL derivatives and/or one or more additional drug or therapeutically active agent. A composition of the disclosure may further comprise a pharmaceutically acceptable excipient, carrier or diluent. Further, a composition of the disclosure may contain preserving agents, solubilizing agents, stabilizing agents, wetting agents, emulsifiers, sweeteners, colorants, odorants, salts (substances of the present disclosure may themselves be provided in the form of a pharmaceutically acceptable salt), buffers, coating agents or antioxidants.

Other aspects of the disclosure are described in further detail below.

(a) Sesquiterpene Lactones (SLs) and SL Derivatives

In general, the compounds detailed herein include compounds comprising a SL structure as diagrammed below. Sesquiterpene lactones (SLs) are a class of chemical compounds characterized as sesquiterpenoids (built from three isoprene units) and contain a lactone ring. Sesquiterpene lactones can be divided into several main classes including germacranolides, heliangolides, guaianolides, pseudoguaianolides, hypocretenolides, and eudesmanolides. A SL or SL derivative of the disclosure may be from the class germacranolide, heliangolide, guaianolide, pseudoguaianolide, hypocretenolide, or eudesmanolide. In an embodiment, a SL or SL derivative of the disclosure is from the class germacranolide or guaianolide. In another embodiment, a SL or SL derivative of the disclosure comprises a polar substituent adjacent to the lactone ring and, optionally, an α-methylene group of the γ-lactone ring. The preferred location of the polar substituent is indicated via the arrow in the diagram below. In an embodiment, a SL or SL derivative of the disclosure comprises a polar substituent adjacent to the lactone ring and an α-methylene group of the γ-lactone ring. In another embodiment, a SL or SL derivative of the disclosure is a germacranolide or guaianolide comprising a polar substituent adjacent to the lactone ring and, optionally, an α-methylene group of the γ-lactone ring. In still another embodiment, a SL or SL derivative of the disclosure is a germacranolide or guaianolide comprising a polar substituent adjacent to the lactone ring and an α-methylene group of the γ-lactone ring. In still yet another embodiment, a SL or SL derivative of the disclosure is a guaianolide comprising a polar substituent adjacent to the lactone ring and, optionally, an α-methylene group of the γ-lactone ring. In yet another embodiment, a SL or SL derivative of the disclosure is a guaianolide comprising a polar substituent adjacent to the lactone ring and an α-methylene group of the γ-lactone ring. In a different embodiment, a SL or SL derivative of the disclosure comprises a methacrylate ester side chain and an α-methylene group of the γ-lactone ring. In another different embodiment, a SL or SL derivative of the disclosure is a germacranolide or guaianolide comprising a methacrylate ester side chain and, optionally, an α-methylene group of the γ-lactone ring. In still another different embodiment, a SL or SL derivative of the disclosure is a germacranolide or guaianolide comprising a methacrylate ester side chain and an α-methylene group of the γ-lactone ring. In still yet another different embodiment, a SL or SL derivative of the disclosure is a guaianolide comprising a methacrylate ester side chain and, optionally, an α-methylene group of the γ-lactone ring. In yet another different embodiment, a SL or SL derivative of the disclosure is a guaianolide comprising a methacrylate ester side chain and an α-methylene group of the γ-lactone ring. In a specific embodiment, a SL of the disclosure is selected from the group consisting of calaxin, eupatoriopicrin, glaucolide E, bahia II, bahia I, and glaucolide A. In another specific embodiment, a SL of the disclosure is calaxin.

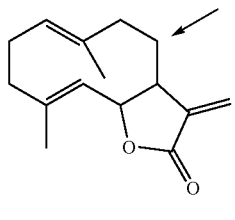

A

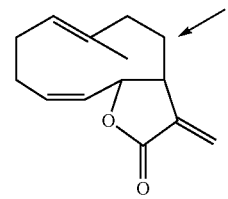

B

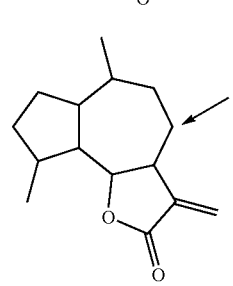

C

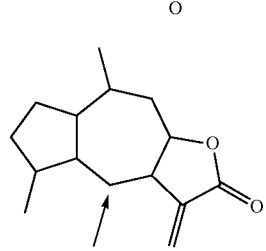

D

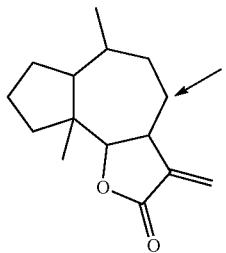

E

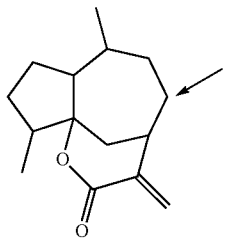

F

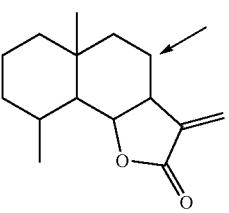

G

A: Germacranolides, B: Heliangolides, C+D: Guaianolides, E: Pseudoguaianolides, F: Hypocretenolides, G: Eudesmanolides.

SLs may be isolated from a variety of plants including, but not limited to, *Laurus nobilis, Chrysanthemum*, pyrethrum, star anise, *Calea ternifolia*, ragweed, sneezeweed, ironweed, sagebrush, wormwood, mugwort, boneset, poverty weed, marsh elder, cocklebur, burdock, chamomile, feverfew, artichoke, gailladrin, *parthenium*, of SLs from plants, SLs may also be produced by organic synthesis.

Also provided herein are derivatives of SLs. SL derivatives are modified versions of SL that are able to react with NF-κB thereby preventing NF-κB from SL derivatives of the disclosure comprise a polar substituent adjacent to the lactone ring (as indicated in the diagram above). In certain embodiments, SL derivatives of the disclosure comprise a methacrylate group adjacent to the lactone ring (as indicated in the diagram above).

As such, provided herein are compounds comprising Formula (I):

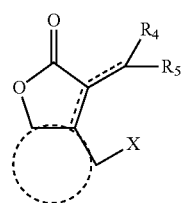

(I)

wherein:
X is a polar substituent;
$R_4$ and $R_5$ are independently selected from the group consisting of hydrogen, hydrocarbyl and substituted hydrocarbyl;

------ is a single or double bond; and

◯ is a SL ring structure, minus the lactone ring, from the class of SLs including germacranolides, heliangolides, guaianolides, pseudoguaianolides, hypocretenolides, and eudesmanolides.

In certain embodiments, the SL ring structure, minus the lactone ring is from the germacranolide class or the guaianolide class. In one embodiment, the SL ring structure, minus the lactone ring is from the germacranolide class. In another embodiment, the SL ring structure, minus the lactone ring is from the guaianolide class.

As used herein, a polar substituent is a substituent comprising at least one atom that modifies electrostatic forces. More specifically, a polar substituent comprises an electronegative atom. In general, electronegativity of an atom increases as one moves right and up across the periodic table of elements. In certain embodiments, the electronegative atom is selected from the group consisting of fluorine, oxygen, nitrogen, chlorine, bromine, and iodine. Accordingly, a compound comprises Formula (I) wherein, X is a substituent comprising an atom selected from the group consisting of fluorine, oxygen, nitrogen, chlorine, bromine, and iodine. In certain embodiments, a compound comprises Formula (I) wherein, X is a substituent comprising an atom selected from the group consisting of oxygen and nitrogen. In a specific embodiment, X is OH.

In an aspect, X is selected from the group consisting of —NR$^{18}$R$^{19}$, —OR$^{18}$, and —NHC(O)R$^{18}$, wherein R$^{18}$ and R$^{19}$ are independently selected from the group consisting of hydrogen, hydrocarbyl and substituted hydrocarbyl. In certain embodiments, R$^{18}$ and R$^{19}$ are independently selected from the group consisting of hydrogen, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl.

In another aspect, a compound of Formula (I) comprises any of the preceding compounds of Formula (I), wherein R$_4$ and R$_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (I) comprises any of the preceding compounds of Formula (I), wherein R$_4$ and R$_5$ are independently selected from the group consisting of hydrogen, —OCOCH$_3$, alkyl, substituted alkyl, ester and substituted ester. In one embodiment, the lactone ring does not contain a double bond, comprises an α-methylene group and R$_4$ and R$_5$ are hydrogen. In another embodiment, the lactone ring contains a double bond, does not comprise an α-methylene group, R$_4$ is hydrogen and R$_5$ is selected from the group consisting of —OCOCH$_3$, alkyl, substituted alkyl, ester and substituted ester. In still another embodiment, the lactone ring contains a double bond, does not comprise an α-methylene group, R$_4$ is hydrogen and R$_5$ is —OCOCH$_3$.

Also provided herein are compounds comprising Formula (Ia):

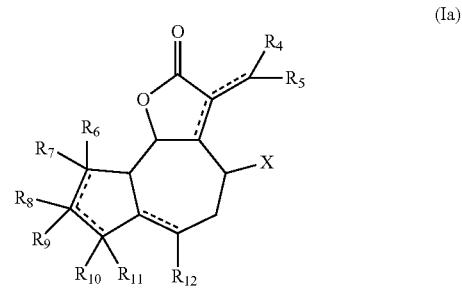

(Ia)

wherein:
X is a polar substituent; R$_4$ and R$_5$ are independently selected from the group consisting of hydrogen, hydrocarbyl and substituted hydrocarbyl;
------ is a single or double bond; and
R$_6$, R$_7$, R$_8$, R$_9$, R$_{10}$, R$_{11}$ and R$_{12}$ are independently selected from the group consisting of hydrogen, hydrocarbyl and substituted hydrocarbyl.

In certain embodiments, a compound comprises Formula (Ia) wherein, X is a substituent comprising an atom selected from the group consisting of fluorine, oxygen, nitrogen, chlorine, bromine, and iodine. In other embodiments, a compound comprises Formula (Ia) wherein, X is a substituent comprising an atom selected from the group consisting of oxygen and nitrogen. In an aspect, X is selected from the group consisting of —NR$^{18}$R$^{19}$, —OR$^{18}$, and —NHC(O)R$^{18}$, wherein R$^{18}$ and R$^{19}$ are independently selected from the group consisting of hydrogen, hydrocarbyl and substituted hydrocarbyl. In certain embodiments, R$^{18}$ and R$^{19}$ are independently selected from the group consisting of hydrogen, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In a specific embodiment, X is OH.

In another aspect, a compound of Formula (Ia) comprises any of the preceding compounds of Formula (Ia), wherein R$_4$ and R$_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (Ia) comprises any of the preceding compounds of Formula (Ia), wherein R$_4$ and R$_5$ are independently selected from the group consisting of hydrogen, —OCOCH$_3$, alkyl, substituted alkyl, ester and substituted ester. In one embodiment, the lactone ring does not contain a double bond, comprises an α-methylene group and R$_4$ and R$_5$ are hydrogen. In another embodiment, the lactone ring contains a double bond, does not comprise an α-methylene group, R$_4$ is hydrogen and R$_5$ is selected from the group consisting of —OCOCH$_3$, alkyl, substituted alkyl, ester and substituted ester. In still another embodiment, the lactone ring contains a double bond, does not comprise an α-methylene group, R$_4$ is hydrogen and R$_5$ is —OCOCH$_3$.

In an aspect, a compound of Formula (Ia) comprises any of the preceding compounds of Formula (Ia), wherein R$_6$ is a C$_1$-C$_6$ alkyl and R$_7$ and R$_8$ form a double bond. In another aspect, a compound of Formula (Ia) comprises any of the preceding compounds of Formula (Ia), wherein R$_6$ is a methyl and R$_7$ and R$_8$ form a double bond. In still another aspect, a compound of Formula (Ia) comprises any of the preceding compounds of Formula (Ia), wherein $R_9$, $R_{10}$, and $R_{11}$ are hydrogen. In still yet another aspect, a compound of Formula (Ia) comprises any of the preceding compounds of Formula (Ia), wherein $R_6$ is a $C_1$-$C_6$ alkyl and $R_7$ and $R_8$ form a double bond and $R_9$, $R_{10}$, and $R_{11}$ are hydrogen. In yet another aspect, a compound of Formula (Ia) comprises any of the preceding compounds of Formula (Ia), wherein $R_6$ is a methyl and $R_7$ and $R_8$ form a double bond and $R_9$, $R_{10}$, and $R_{11}$ are hydrogen. In a different, a compound of Formula (Ia) comprises any of the preceding compounds of Formula (Ia), wherein $R_{12}$ forms an epoxide ring.

Also provided herein are compounds comprising Formula (Ib):

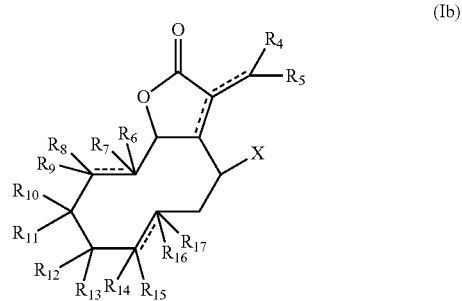

(Ib)

wherein:
X is a polar substituent;
$R_4$ and $R_5$ are independently selected from the group consisting of hydrogen, hydrocarbyl and substituted hydrocarbyl;
----- is a single or double bond; and
$R_6$, $R_7$, $R_8$, $R_9$, $R_{10}$, $R_{11}$, $R_{12}$, $R_{13}$, $R_{14}$, $R_{15}$, $R_{16}$ and $R_{17}$ are independently selected from the group consisting of hydrogen, hydrocarbyl and substituted hydrocarbyl.

In certain embodiments, a compound comprises Formula (Ib) wherein, X is a substituent comprising an atom selected from the group consisting of fluorine, oxygen, nitrogen, chlorine, bromine, and iodine. In other embodiments, a compound comprises Formula (Ib) wherein, X is a substituent comprising an atom selected from the group consisting of oxygen and nitrogen. In an aspect, X is selected from the group consisting of —$NR^{18}R^{19}$, —$OR^{18}$, and —NHC(O)$R^{18}$, wherein $R^{18}$ and $R^{19}$ are independently selected from the group consisting of hydrogen, hydrocarbyl and substituted hydrocarbyl. In certain embodiments, $R^{18}$ and $R^{19}$ are independently selected from the group consisting of hydrogen, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In a specific embodiment, X is OH.

In another aspect, a compound of Formula (Ib) comprises any of the preceding compounds of Formula (Ib), wherein $R_4$ and $R_5$ are independently selected from the group consisting of hydrogen, —$OCOCH_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (Ib) comprises any of the preceding compounds of Formula (Ib), wherein $R_4$ and $R_5$ are independently selected from the group consisting of hydrogen, —$OCOCH_3$, alkyl, substituted alkyl, ester and substituted ester. In one embodiment, the lactone ring does not contain a double bond, comprises an α-methylene group and $R_4$ and $R_5$ are hydrogen. In another embodiment, the lactone ring contains a double bond, does not comprise an α-methylene group, $R_4$ is hydrogen and $R_5$ is selected from the group consisting of —$OCOCH_3$, alkyl, substituted alkyl, ester and substituted ester. In still another embodiment, the lactone ring contains a double bond, does not comprise an α-methylene group, $R_4$ is hydrogen and $R_5$ is —$OCOCH_3$.

In an aspect, a compound of Formula (Ib) comprises any of the preceding compounds of Formula (Ib), wherein $R_7$ and $R_8$ form an epoxide ring or $R_7$ and $R_8$ form a double bond. In another aspect, a compound of Formula (Ib) comprises any of the preceding compounds of Formula (Ib), wherein $R_9$ is a $C_1$-$C_6$ alkyl. In still another aspect, a compound of Formula (Ib) comprises any of the preceding compounds of Formula (Ib), wherein $R_9$ is a methyl. In yet still another aspect, a compound of Formula (Ib) comprises any of the preceding compounds of Formula (Ib), wherein $R_{12}$ is OC(O)$CH_3$. In a different aspect, a compound of Formula (Ib) comprises any of the preceding compounds of Formula (Ib), wherein $R_{17}$ is a $C_1$-$C_6$ alkyl. In another different aspect, a compound of Formula (Ib) comprises any of the preceding compounds of Formula (Ib), wherein $R_{17}$ is a methyl. In other aspects, a compound of Formula (Ib) comprises any of the preceding compounds of Formula (Ib), wherein $R_{15}$ and $R_{16}$ forms a double bond. In various aspects, a compound of Formula (Ib) comprises any of the preceding compounds of Formula (Ib), wherein $R_6$, $R_{10}$, $R_{11}$, $R_{12}$, $R_{13}$, $R_{14}$ are independently hydrogen.

Also provided herein are compounds comprising Formula (Ic):

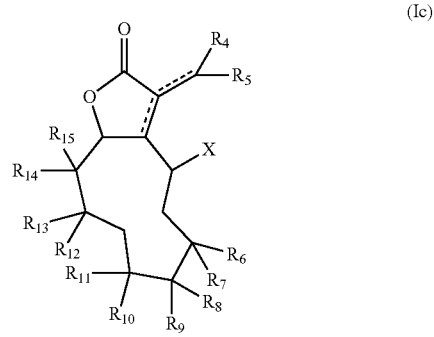

(Ic)

wherein:
X is a polar substituent;
$R_4$ and $R_5$ are independently selected from the group consisting of hydrogen, hydrocarbyl and substituted hydrocarbyl;
----- is a single or double bond; and
$R_6$, $R_7$, $R_8$, $R_9$, $R_{10}$, $R_{11}$, $R_{12}$, $R_{13}$, $R_{14}$ and $R_{15}$ are independently selected from the group consisting of hydrogen, hydrocarbyl and substituted hydrocarbyl.

In certain embodiments, a compound comprises Formula (Ic) wherein, X is a substituent comprising an atom selected from the group consisting of fluorine, oxygen, nitrogen, chlorine, bromine, and iodine. In other embodiments, a compound comprises Formula (Ic) wherein, X is a substituent comprising an atom selected from the group consisting of oxygen and nitrogen. In an aspect, X is selected from the group consisting of —$NR^{18}R^{19}$, —$OR^{18}$, and —NHC(O)$R^{18}$, wherein $R^{18}$ and $R^{19}$ are independently selected from the group consisting of hydrogen, hydrocarbyl and substituted hydrocarbyl. In certain embodiments, $R^{18}$ and $R^{19}$ are independently selected from the group consisting of hydrogen, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In a specific embodiment, X is OH.

In another aspect, a compound of Formula (Ic) comprises any of the preceding compounds of Formula (Ic), wherein $R_4$ and $R_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (Ic) comprises any of the preceding compounds of Formula (Ic), wherein $R_4$ and $R_5$ are independently selected from the group consisting of hydrogen, —OCOCH$_3$, alkyl, substituted alkyl, ester and substituted ester. In one embodiment, the lactone ring does not contain a double bond, comprises an α-methylene group and $R_4$ and $R_5$ are hydrogen. In another embodiment, the lactone ring contains a double bond, does not comprise an α-methylene group, $R_4$ is hydrogen and $R_5$ is selected from the group consisting of —OCOCH$_3$, alkyl, substituted alkyl, ester and substituted ester. In still another embodiment, the lactone ring contains a double bond, does not comprise an α-methylene group, $R_4$ is hydrogen and $R_5$ is OCOCH$_3$.

In an aspect, a compound of Formula (Ic) comprises any of the preceding compounds of Formula (Ic), wherein $R_{13}$ and $R_{14}$ form an epoxide ring. In another aspect, a compound of Formula (Ic) comprises any of the preceding compounds of Formula (Ic), wherein $R_{12}$ is a $C_1$-$C_6$ alkyl. In still another aspect, a compound of Formula (Ic) comprises any of the preceding compounds of Formula (Ic), wherein $R_{12}$ is a methyl. In still yet another aspect, a compound of Formula (Ic) comprises any of the preceding compounds of Formula (Ic), wherein $R_8$ and $R_9$ form an oxo group. In yet another aspect, a compound of Formula (Ic) comprises any of the preceding compounds of Formula (Ic), wherein $R_7$ is OC(O)CH$_3$ and $R_6$ is a $C_1$-$C_6$ alkyl. In a different aspect, a compound of Formula (Ic) comprises any of the preceding compounds of Formula (Ic), wherein $R_7$ is OC(O)CH$_3$ and $R_6$ is a methyl. In other aspects, a compound of Formula (Ic) comprises any of the preceding compounds of Formula (Ic), wherein $R_{10}$ and $R_{11}$ are hydrogen.

Also provided herein are compounds comprising Formula (Id):

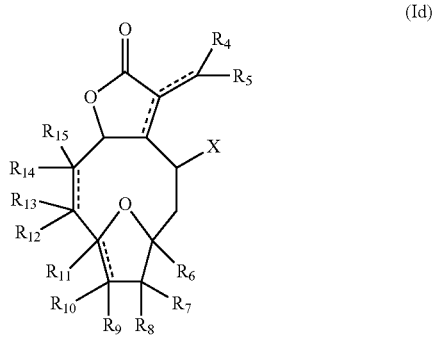

wherein:
X is a polar substituent;
$R_4$ and $R_5$ are independently selected from the group consisting of hydrogen, hydrocarbyl and substituted hydrocarbyl;
----- is a single or double bond; and
$R_6$, $R_7$, $R_8$, $R_9$, $R_{10}$, $R_{11}$, $R_{12}$, $R_{13}$, $R_{14}$ and $R_{15}$ are independently selected from the group consisting of hydrogen, hydrocarbyl and substituted hydrocarbyl.

In certain embodiments, a compound comprises Formula (Id) wherein, X is a substituent comprising an atom selected from the group consisting of fluorine, oxygen, nitrogen, chlorine, bromine, and iodine. In other embodiments, a compound comprises Formula (Id) wherein, X is a substituent comprising an atom selected from the group consisting of oxygen and nitrogen. In an aspect, X is selected from the group consisting of —NR$^{18}$R$^{19}$, —OR$^{18}$, and —NHC(O)R$^{18}$, wherein R$^{18}$ and R$^{19}$ are independently selected from the group consisting of hydrogen, hydrocarbyl and substituted hydrocarbyl. In certain embodiments, R$^{18}$ and R$^{19}$ are independently selected from the group consisting of hydrogen, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In a specific embodiment, X is OH.

In another aspect, a compound of Formula (Id) comprises any of the preceding compounds of Formula (Id), wherein $R_4$ and $R_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (Id) comprises any of the preceding compounds of Formula (Id), wherein $R_4$ and $R_5$ are independently selected from the group consisting of hydrogen, —OCOCH$_3$, alkyl, substituted alkyl, ester and substituted ester. In one embodiment, the lactone ring does not contain a double bond, comprises an α-methylene group and $R_4$ and $R_5$ are hydrogen. In another embodiment, the lactone ring contains a double bond, does not comprise an α-methylene group, $R_4$ is hydrogen and $R_5$ is selected from the group consisting of —OCOCH$_3$, alkyl, substituted alkyl, ester and substituted ester. In still another embodiment, the lactone ring contains a double bond, does not comprise an α-methylene group, $R_4$ is hydrogen and $R_5$ is —OCOCH$_3$.

In an aspect, a compound of Formula (Id) comprises any of the preceding compounds of Formula (Id), wherein $R_6$ is a $C_1$-$C_6$ alkyl. In another aspect, a compound of Formula (Id) comprises any of the preceding compounds of Formula (Id), wherein $R_6$ is a methyl. In still another aspect, a compound of Formula (Id) comprises any of the preceding compounds of Formula (Id), wherein $R_7$ and $R_8$ form an oxo group. In still yet another aspect, a compound of Formula (Id) comprises any of the preceding compounds of Formula (Id), wherein $R_{10}$ and $R_{11}$ form a double bond. In yet another aspect, a compound of Formula (Id) comprises any of the preceding compounds of Formula (Id), wherein $R_{12}$ is a $C_1$-$C_6$ alkyl. In a different aspect, a compound of Formula (Id) comprises any of the preceding compounds of Formula (Id), wherein $R_{12}$ is a methyl. In other aspects, a compound of Formula (Id) comprises any of the preceding compounds of Formula (Id), wherein $R_{13}$ and $R_{14}$ form a double bond. In various aspects, a compound of Formula (Id) comprises any of the preceding compounds of Formula (Id), wherein $R_9$ and $R_{15}$ are hydrogen.

Additionally, provided herein are compounds comprising Formula (II):

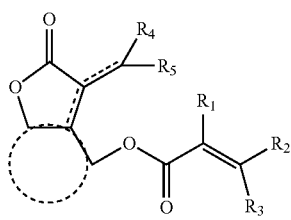

(II)

wherein:

R$_1$, R$_2$ and R$_3$ are independently selected from the group consisting of hydrogen, hydrocarbyl and substituted hydrocarbyl;

R$_4$ and R$_5$ are independently selected from the group consisting of hydrogen, hydrocarbyl and substituted hydrocarbyl;

----- is a single or double bond; and

◌ is a SL ring structure, minus the lactone ring, from the class of SLs including germacranolides, heliangolides, guaianolides, pseudoguaianolides, hypocretenolides, and eudesmanolides.

In certain embodiments, the SL ring structure, minus the lactone ring is from the germacranolide class or the guaianolide class. In one embodiment, the SL ring structure, minus the lactone ring is from the germacranolide class. In another embodiment, the SL ring structure, minus the lactone ring is from the guaianolide class.

In some embodiments, R$_1$, R$_2$ and R$_3$ are independently selected from the group consisting of hydrogen, CH$_3$, CH$_2$OH, alkoxy, hydroxyalkyl, carbonylalkyl, carbonyl substituted alkyl, carbonylalkoxy, carbonylaminoalkyl, alkyl, substituted alkyl, alkenyl, substituted alkenyl, alkynyl and substituted alkynyl. In other embodiments, R$_1$, R$_2$ and R$_3$ are independently selected from the group consisting of hydrogen, CH$_3$, CH$_2$OH, alkyl and substituted alkyl. In other embodiments, R$_1$ is CH$_3$ and R$_2$ and R$_3$ are hydrogen. Alternatively, R$_1$ and R$_2$ are CH$_2$OH and R$_3$ is hydrogen.

In another embodiment, a compound of Formula (II) comprises any of the preceding compounds of Formula (II), wherein R$_4$ and R$_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (II) comprises any of the preceding compounds of Formula (II), wherein R$_4$ and R$_5$ are independently selected from the group consisting of hydrogen, —OCOCH$_3$, alkyl, substituted alkyl, ester and substituted ester. In one embodiment, the lactone ring does not contain a double bond, comprises an α-methylene group and R$_4$ and R$_5$ are hydrogen. In another embodiment, the lactone ring contains a double bond, does not comprise an α-methylene group, R$_4$ is hydrogen and R$_5$ is selected from the group consisting of —OCOCH$_3$, alkyl, substituted alkyl, ester and substituted ester. In still another embodiment, the lactone ring contains a double bond, does not comprise an α-methylene group, R$_4$ is hydrogen and R$_5$ is —OCOCH$_3$.

Also provided herein are compounds comprising Formula (IIa):

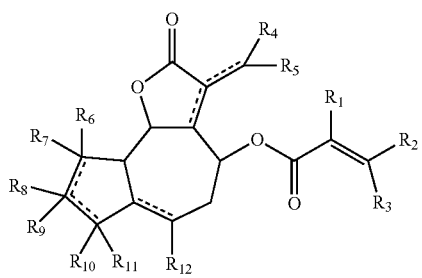

(IIa)

wherein:

R$_1$, R$_2$ and R$_3$ are independently selected from the group consisting of hydrogen, hydrocarbyl and substituted hydrocarbyl;

R$_4$ and R$_5$ are independently selected from the group consisting of hydrogen, hydrocarbyl and substituted hydrocarbyl;

----- is a single or double bond; and

R$_6$, R$_7$, R$_8$, R$_9$, R$_{10}$, R$_{11}$ and R$_{12}$ are independently selected from the group consisting of hydrogen, hydrocarbyl and substituted hydrocarbyl.

In some embodiments, R$_1$, R$_2$ and R$_3$ are independently selected from the group consisting of hydrogen, CH$_3$, CH$_2$OH, alkoxy, hydroxyalkyl, carbonylalkyl, carbonyl substituted alkyl, carbonylalkoxy, carbonylaminoalkyl, alkyl, substituted alkyl, alkenyl, substituted alkenyl, alkynyl and substituted alkynyl. In other embodiments, R$_1$, R$_2$ and R$_3$ are independently selected from the group consisting of hydrogen, CH$_3$, CH$_2$OH, alkyl and substituted alkyl. In other embodiments, R$_1$ is CH$_3$ and R$_2$ and R$_3$ are hydrogen. Alternatively, R$_1$ and R$_2$ are CH$_2$OH and R$_3$ is hydrogen.

In another embodiment, a compound of Formula (IIa) comprises any of the preceding compounds of Formula (IIa), wherein R$_4$ and R$_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (IIa) comprises any of the preceding compounds of Formula (IIa), wherein R$_4$ and R$_5$ are independently selected from the group consisting of hydrogen, —OCOCH$_3$, alkyl, substituted alkyl, ester and substituted ester. In one embodiment, the lactone ring does not contain a double bond, comprises an α-methylene group and R$_4$ and R$_5$ are hydrogen. In another embodiment, the lactone ring contains a double bond, does not comprise an α-methylene group, R$_4$ is hydrogen and R$_5$ is selected from the group consisting of —OCOCH$_3$, alkyl, substituted alkyl, ester and substituted ester. In still another embodiment, the lactone ring contains a double bond, does not comprise an α-methylene group, R$_4$ is hydrogen and R$_5$ is —OCOCH$_3$.

In an aspect, a compound of Formula (IIa) comprises any of the preceding compounds of Formula (IIa), wherein R$_6$ is a C$_1$-C$_6$ alkyl and R$_7$ and R$_8$ form a double bond. In another aspect, a compound of Formula (IIa) comprises any of the preceding compounds of Formula (IIa), wherein R$_6$ is a methyl and R$_7$ and R$_8$ form a double bond. In still another aspect, a compound of Formula (IIa) comprises any of the preceding compounds of Formula (IIa), wherein R$_9$, R$_{10}$, and $R_{11}$ are hydrogen. In still yet another aspect, a compound of Formula (IIa) comprises any of the preceding compounds of Formula (IIa), wherein $R_6$ is a $C_1$-$C_6$ alkyl and $R_7$ and $R_8$ form a double bond and $R_9$, $R_{10}$, and $R_{11}$ are hydrogen. In yet another aspect, a compound of Formula (IIa) comprises any of the preceding compounds of Formula (IIa), wherein $R_6$ is a methyl and $R_7$ and $R_8$ form a double bond and $R_9$, $R_{10}$, and $R_{11}$ are hydrogen. In a different, a compound of Formula (IIa) comprises any of the preceding compounds of Formula (IIa), wherein $R_{12}$ forms an epoxide ring.

Also provided herein are compounds comprising Formula (IIb):

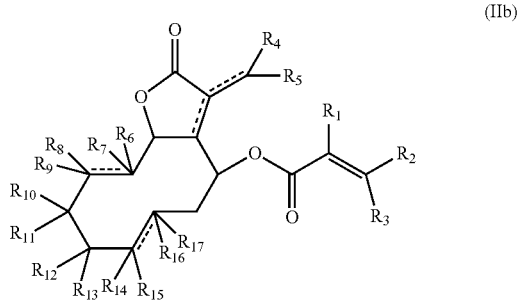

wherein:
$R_1$, $R_2$ and $R_3$ are independently selected from the group consisting of hydrogen, hydrocarbyl and substituted hydrocarbyl;
$R_4$ and $R_5$ are independently selected from the group consisting of hydrogen, hydrocarbyl and substituted hydrocarbyl;
----- is a single or double bond; and
$R_6$, $R_7$, $R_8$, $R_9$, $R_{10}$, $R_{11}$, $R_{12}$, $R_{13}$, $R_{14}$, $R_{15}$, $R_{16}$ and $R_{17}$ are independently selected from the group consisting of hydrogen, hydrocarbyl and substituted hydrocarbyl.

In some embodiments, $R_1$, $R_2$ and $R_3$ are independently selected from the group consisting of hydrogen, $CH_3$, $CH_2OH$, alkoxy, hydroxyalkyl, carbonylalkyl, carbonyl substituted alkyl, carbonylalkoxy, carbonylaminoalkyl, alkyl, substituted alkyl, alkenyl, substituted alkenyl, alkynyl and substituted alkynyl. In other embodiments, $R_1$, $R_2$ and $R_3$ are independently selected from the group consisting of hydrogen, $CH_3$, $CH_2OH$, alkyl and substituted alkyl. In other embodiments, $R_1$ is $CH_3$ and $R_2$ and $R_3$ are hydrogen. Alternatively, $R_1$ and $R_2$ are $CH_2OH$ and $R_3$ is hydrogen.

In another embodiment, a compound of Formula (IIb) comprises any of the preceding compounds of Formula (IIb), wherein $R_4$ and $R_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (IIb) comprises any of the preceding compounds of Formula (IIb), wherein $R_4$ and $R_5$ are independently selected from the group consisting of hydrogen, —OCOCH$_3$, alkyl, substituted alkyl, ester and substituted ester. In one embodiment, the lactone ring does not contain a double bond, comprises an α-methylene group and $R_4$ and $R_5$ are hydrogen. In another embodiment, the lactone ring contains a double bond, does not comprise an α-methylene group, $R_4$ is hydrogen and $R_5$ is selected from the group consisting of —OCOCH$_3$, alkyl, substituted alkyl, ester and substituted ester. In still another embodiment, the lactone ring contains a double bond, does not comprise an α-methylene group, $R_4$ is hydrogen and $R_5$ is —OCOCH$_3$.

In an aspect, a compound of Formula (IIb) comprises any of the preceding compounds of Formula (IIb), wherein $R_7$ and $R_8$ form an epoxide ring or $R_7$ and $R_8$ form a double bond. In another aspect, a compound of Formula (IIb) comprises any of the preceding compounds of Formula (IIb), wherein $R_9$ is a $C_1$-$C_6$ alkyl. In still another aspect, a compound of Formula (IIb) comprises any of the preceding compounds of Formula (IIb), wherein $R_9$ is a methyl. In yet still another aspect, a compound of Formula (IIb) comprises any of the preceding compounds of Formula (IIb), wherein $R_{12}$ is OC(O)CH$_3$. In a different aspect, a compound of Formula (IIb) comprises any of the preceding compounds of Formula (IIb), wherein $R_{17}$ is a $C_1$-$C_6$ alkyl. In another different aspect, a compound of Formula (IIb) comprises any of the preceding compounds of Formula (IIb), wherein $R_{17}$ is a methyl. In other aspects, a compound of Formula (IIb) comprises any of the preceding compounds of Formula (IIb), wherein $R_{15}$ and $R_{16}$ forms a double bond. In various aspects, a compound of Formula (IIb) comprises any of the preceding compounds of Formula (IIb), wherein $R_6$, $R_{10}$, $R_{11}$, $R_{12}$, $R_{13}$, $R_{14}$ are independently hydrogen.

Also provided herein are compounds comprising Formula (IIc):

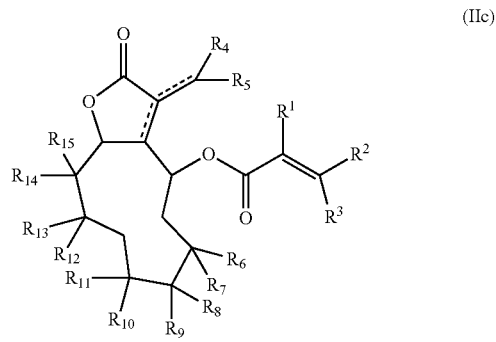

wherein:
$R_1$, $R_2$ and $R_3$ are independently selected from the group consisting of hydrogen, hydrocarbyl and substituted hydrocarbyl;
$R_4$ and $R_5$ are independently selected from the group consisting of hydrogen, hydrocarbyl and substituted hydrocarbyl;
----- is a single or double bond; and
$R_6$, $R_7$, $R_8$, $R_9$, $R_{10}$, $R_{11}$, $R_{12}$, $R_{13}$, $R_{14}$ and $R_{15}$ are independently selected from the group consisting of hydrogen, hydrocarbyl and substituted hydrocarbyl.

In some embodiments, $R_1$, $R_2$ and $R_3$ are independently selected from the group consisting of hydrogen, $CH_3$, $CH_2OH$, alkoxy, hydroxyalkyl, carbonylalkyl, carbonyl substituted alkyl, carbonylalkoxy, carbonylaminoalkyl, alkyl, substituted alkyl, alkenyl, substituted alkenyl, alkynyl and substituted alkynyl. In other embodiments, $R_1$, $R_2$ and $R_3$ are independently selected from the group consisting of hydrogen, $CH_3$, $CH_2OH$, alkyl and substituted alkyl. In other embodiments, $R_1$ is $CH_3$ and $R_2$ and $R_3$ are hydrogen. Alternatively, $R_1$ and $R_2$ are $CH_2OH$ and $R_3$ is hydrogen.

In another embodiment, a compound of Formula (IIc) comprises any of the preceding compounds of Formula (IIc), wherein $R_4$ and $R_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (IIc) comprises any of the preceding compounds of Formula (IIc), wherein R$_4$ and R$_5$ are independently selected from the group consisting of hydrogen, —OCOCH$_3$, alkyl, substituted alkyl, ester and substituted ester. In one embodiment, the lactone ring does not contain a double bond, comprises an α-methylene group and R$_4$ and R$_5$ are hydrogen. In another embodiment, the lactone ring contains a double bond, does not comprise an α-methylene group, R$_4$ is hydrogen and R$_5$ is selected from the group consisting of —OCOCH$_3$, alkyl, substituted alkyl, ester and substituted ester. In still another embodiment, the lactone ring contains a double bond, does not comprise an α-methylene group, R$_4$ is hydrogen and R$_5$ is —OCOCH$_3$.

In an aspect, a compound of Formula (IIc) comprises any of the preceding compounds of Formula (IIc), wherein R$_{13}$ and R$_{14}$ form an epoxide ring. In another aspect, a compound of Formula (IIc) comprises any of the preceding compounds of Formula (IIc), wherein R$_{12}$ is a C$_1$-C$_6$ alkyl. In still another aspect, a compound of Formula (IIc) comprises any of the preceding compounds of Formula (IIc), wherein R$_{12}$ is a methyl. In still yet another aspect, a compound of Formula (IIc) comprises any of the preceding compounds of Formula (IIc), wherein R$_8$ and R$_9$ form an oxo group. In yet another aspect, a compound of Formula (IIc) comprises any of the preceding compounds of Formula (IIc), wherein R$_7$ is OC(O)CH$_3$ and R$_6$ is a C$_1$-C$_6$ alkyl. In a different aspect, a compound of Formula (IIc) comprises any of the preceding compounds of Formula (IIc), wherein R$_7$ is OC(O)CH$_3$ and R$_6$ is a methyl. In other aspects, a compound of Formula (IIc) comprises any of the preceding compounds of Formula (IIc), wherein R$_{10}$ and R$_{11}$ are hydrogen.

Also provided herein are compounds comprising Formula (IId):

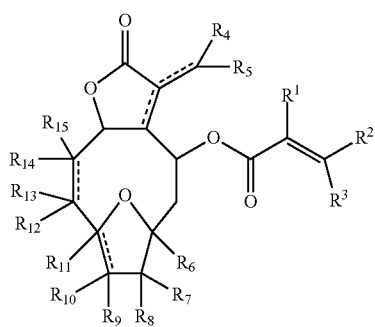

(IId)

wherein:
R$_1$, R$_2$ and R$_3$ are independently selected from the group consisting of hydrogen, hydrocarbyl and substituted hydrocarbyl;
R$_4$ and R$_5$ are independently selected from the group consisting of hydrogen, hydrocarbyl and substituted hydrocarbyl;
===== is a single or double bond; and
R$_6$, R$_7$, R$_8$, R$_9$, R$_{10}$, R$_{11}$, R$_{12}$, R$_{13}$, R$_{14}$ and R$_{15}$ are independently selected from the group consisting of hydrogen, hydrocarbyl and substituted hydrocarbyl.

In some embodiments, R$_1$, R$_2$ and R$_3$ are independently selected from the group consisting of hydrogen, CH$_3$, CH$_2$OH, alkoxy, hydroxyalkyl, carbonylalkyl, carbonyl substituted alkyl, carbonylalkoxy, carbonylaminoalkyl, alkyl, substituted alkyl, alkenyl, substituted alkenyl, alkynyl and substituted alkynyl. In other embodiments, R$_1$, R$_2$ and R$_3$ are independently selected from the group consisting of hydrogen, CH$_3$, CH$_2$OH, alkyl and substituted alkyl. In other embodiments, R$_1$ is CH$_3$ and R$_2$ and R$_3$ are hydrogen. Alternatively, R$_1$ and R$_2$ are CH$_2$OH and R$_3$ is hydrogen.

In another embodiment, a compound of Formula (IId) comprises any of the preceding compounds of Formula (IId), wherein R$_4$ and R$_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl. In still another embodiment, a compound of Formula (IId) comprises any of the preceding compounds of Formula (IId), wherein R$_4$ and R$_5$ are independently selected from the group consisting of hydrogen, —OCOCH$_3$, alkyl, substituted alkyl, ester and substituted ester. In one embodiment, the lactone ring does not contain a double bond, comprises an α-methylene group and R$_4$ and R$_5$ are hydrogen. In another embodiment, the lactone ring contains a double bond, does not comprise an α-methylene group, R$_4$ is hydrogen and R$_5$ is selected from the group consisting of —OCOCH$_3$, alkyl, substituted alkyl, ester and substituted ester. In still another embodiment, the lactone ring contains a double bond, does not comprise an α-methylene group, R$_4$ is hydrogen and R$_5$ is —OCOCH$_3$.

In an aspect, a compound of Formula (IId) comprises any of the preceding compounds of Formula (IId), wherein R$_6$ is a C$_1$-C$_6$ alkyl. In another aspect, a compound of Formula (IId) comprises any of the preceding compounds of Formula (IId), wherein R$_6$ is a methyl. In still another aspect, a compound of Formula (IId) comprises any of the preceding compounds of Formula (IId), wherein R$_7$ and R$_8$ form an oxo group. In still yet another aspect, a compound of Formula (IId) comprises any of the preceding compounds of Formula (IId), wherein R$_{10}$ and R$_{11}$ form a double bond. In yet another aspect, a compound of Formula (IId) comprises any of the preceding compounds of Formula (IId), wherein R$_{12}$ is a C$_1$-C$_6$ alkyl. In a different aspect, a compound of Formula (IId) comprises any of the preceding compounds of Formula (IId), wherein R$_{12}$ is a methyl. In other aspects, a compound of Formula (IId) comprises any of the preceding compounds of Formula (IId), wherein R$_{13}$ and R$_{14}$ form a double bond. In various aspects, a compound of Formula (IId) comprises any of the preceding compounds of Formula (IId), wherein R$_9$ and R$_{15}$ are hydrogen.

(b) Components of the Composition

The present disclosure also provides pharmaceutical compositions. The pharmaceutical composition comprises SL or a SL derivative, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising SL or a SL derivative is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present disclosure. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the SL or a SL derivative in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the SL or a SL derivative may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidyletha-nolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretra-decanoate (myristate), n-hexadecanoate (palmitate), n-octa-decanoate (stearate), n-eicosanoate (arachidate), n-doco-sanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-ei-cosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmi-toyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-diole-olyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbo-cyanine methanesulfonate, N-4-(delinoleylaminostyryl)-N-methylpyridinium iodide, or 1,1,-dilinoleyl-3,3,3',3'-tetram-ethylindocarbocyanine perchloarate.

Liposomes may optionally comprise sphingolipids, in which sphingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethyl-sulfoxide (DMSO), methylpyrrolidone, N-methylpyrroli-done, acetronitrile, alcohols, dimethylformamide, tetrahy-drofuran, or combinations thereof.

Liposomes carrying the SL or SL derivative (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied.

These parameters include, but are not limited to, temperature, pH, concentration of methionine compound, concentration and composition of lipid, concentration of multivalent cations, rate of mixing, presence of and concentration of solvent.

In another embodiment, a composition of the disclosure may be delivered to a cell as a microemulsion, nanoemulsion or self-emulsifying system. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the disclosure generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The SL or SL derivative may be encapsulated in a microemulsion by any method generally known in the art. Nanoemulsions have a 20 to 500 nm size range and are kinetically stable, and self-emulsifying systems form spontaneously without agitation.

In yet another embodiment, a SL or a SL derivative may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the disclosure. Generally, the size of dendrimers may range from about 1 nm to about 100 nm.

II. Process of Synthesizing SL or SL Derivatives

In another aspect, the disclosure provides a method of making SL or SL derivatives disclosed herein. The general synthetic procedure is provided in the schematic below:

Accordingly, using the methods provided above SL derivatives comprising a polar substituent adjacent to the lactone ring may be synthesized Specifically, the polar substituent comprises nitrogen or oxygen. In certain embodiments, the starting SL product is from the germacranolide or guaianolide class. In other embodiments, the starting SL product is Bahia.

For example, when the starting product is Bahia II, Bahia I may be synthesized. Specifically, a mixture of bahia II (0.13 mmol), 1 mL of methanol and 10 mL of aqueous LiOH (1.3 mmol) may be stirred at room temperature for an hour. The pH of the reaction mixture may be adjusted to 5 using acetic acid and then the compound may be extracted with ethyl acetate. The organic layer may be dried using anhydrous sodium carbonate, evaporated under reduced pressure and the residue may be further purified by column chromatography (silica gel, ethyl acetate). The resulting compound may be crystallized using acetone-isopropyl to yield Bahia I. The described synthetic method is depicted below:

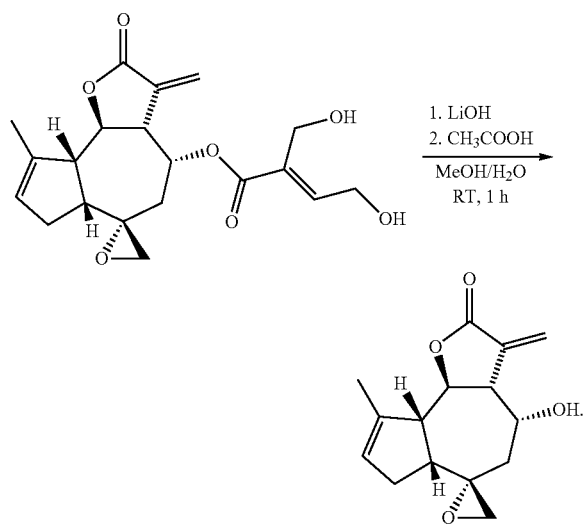

III. Methods

A further aspect of the present disclosure provides a method for inhibiting growth of a cancer cell derived from a blood cancer. More specifically, a method for inhibiting growth of a leukemic cancer cell. For example, a leukemic cancer cell derived from acute myeloid leukemia, chronic myeloid leukemia, chronic lymphocytic leukemia, acute lymphoblastic leukemia, multiple myeloma, myelodysplastic syndrome and myeloproliferative neoplasms. Cancer cell growth includes cell proliferation and cell metastasis. The method comprises contacting the cancer cell with an effective amount of a composition comprising a SL or a SL derivative, wherein the amount is effective to inhibit growth of the cancer cell. Compositions comprising a SL or a SL derivative are detailed above in Section I. In an embodiment, a SL or SL derivative of the disclosure comprises a polar substituent adjacent to the lactone ring and, optionally, an α-methylene group of the γ-lactone ring. In another embodiment, a SL or SL derivative of the disclosure is a germacranolide or guaianolide comprising a polar substituent adjacent to the lactone ring and, optionally, an α-methylene group of the γ-lactone ring. In a different embodiment, a SL or SL derivative of the disclosure comprises a methacrylate ester side chain and, optionally, an α-methylene group of the γ-lactone ring. In another different embodiment, a SL or SL derivative of the disclosure is a germacranolide or guaianolide comprising a methacrylate ester side chain and, optionally, an α-methylene group of the γ-lactone ring. In a specific embodiment, a composition comprises a SL selected from the group consisting of calaxin, eupatoriopicrin, glaucolide E, bahia II, bahia I, and glaucolide A. In another specific embodiment, a composition comprises calaxin.

(a) Contacting the Cell

In some embodiments, the cancer cell may be in vitro. The cancer cell may be an established, commercially-available cancer cell line (e.g., American Type Culture Collection (ATCC), Manassas, Va.). The cancer cell line may be derived from a blood cancer. The cancer cell line may be a human cell line or a mammalian cell line. In a specific embodiment, the cancer cell line may be derived from a blood cancer. In one exemplary embodiment, the cancer cell line may be derived from a leukemic cell. The leukemic cell may be an acute myeloid leukemia cell, a chronic myeloid leukemia cell, an acute lymphocytic leukemia cell, a chronic lymphocytic leukemia cell, a cutaneous T cell leukemia, a leukemia stem cell, or another type of leukemia cell. In a specific embodiment, the leukemic cell may be an acute myeloid leukemia cell. In some embodiments, the cancer cell line may be a leukemia cell line such as Kasumi-1, KCL22, KG-1, MV4-11, MOLM-13, TF-1, THP-1, TUR, HL-60, U937, CCRF-CEM, K-562 or RPMI-8226. In a specific embodiment, the cancer cell line may be MV4-11. In other embodiments, the cancer cell line may be a hematopoietic or lymphoid cell line. Non-limiting examples of hematopoietic or lymphoid cell lines include 380, 697, A3-KAW, A3/KAW, A4-Fuk, A4/Fuk, ALL-PO, ALL-SIL, AML-193, AMO-1, ARH-77, ATN-1, BALL-1, BC-3, BCP-1, BDCM, BE-13, BL-41, BL-70, BV-173, C8166, CA46, CCRF-CEM, CI-1, CMK, CMK-11-5, CMK-86, CML-T1, COLO 775, COLO-677, CTB-1, CTV-1, Daudi, DB, DEL, DG-75, DND-41, DOHH-2, EB1, EB2, EHEB, EJM, EM-2, EOL-1, EoL-1-cell, F-36P, GA-10, GA-10-Clone-4, GDM-1, GR-ST, GRANTA-519, H9, HAL-01, HD-MY-Z, HDLM-2, HEL, HEL 92.1.7, HH, HL-60, HPB-ALL, Hs 604.T, Hs 611.T, Hs 616.T, Hs 751.T, HT, HTK-, HuNS1, HuT 102, HuT 78, IM-9, J-RT3-T3-5, JeKo-1, JiyoyeP-2003, JJN-3, JK-1, JM1, JURKAT, JURL-MK1, JVM-2, JVM-3, K-562, K052, KARPAS-299, KARPAS-422, KARPAS-45, KARPAS-620, KASUMI-1, KASUMI-2, Kasumi-6, KCL-22, KE-37, KE-97, KG-1, KHM-1B, Ki-JK, KM-H2, KMM-1, KMOE-2, KMS-11, KMS-12-BM, KMS-12-PE, KMS-18, KMS-20, KMS-21BM, KMS-26, KMS-27, KMS-28BM, KMS-34, KO52, KOPN-8, KU812, KY821, KYO-1, L-1236, L-363, L-428, L-540, *LAMA*-84, LC4-1, Loucy, LOUCY, LP-1, M-07e, MC-CAR, MC116, ME-1, MEC-1, MEC-2, MEG-01, MHH-CALL-2, MHH-CALL-3, MHH-CALL-4, MHH-PREB-1, Mino, MJ, ML-2, MLMA, MM1-S, MN-60, MOLM-13, MOLM-16, MOLM-6, MOLP-2, MOLP-8, MOLT-13, MOLT-16, MOLT-4, MONO-MAC-1, MONO-MAC-6, MOTN-1, MUTZ-1, MUTZ-3, MUTZ-5, MV-4-11, NALM-1, NALM-19, NALM-6, NAMALWA, NB-4, NCI-H929, NCO2, NKM-1, NOMO-1, NU-DHL-1, NU-DUL-1, OCI-AML2, OCI-AML3, OCI-AML5, OCI-LY-19, OCI-LY10, OCI-LY3, OCI-M1, OPM-2, P12-ICHIKAWA, P30-OHK, P31-FUJ, P31/FUJ, P3HR-1, PCM6, PEER, PF-382, Pfeiffer, PL-21, Raji, Ramos-2G6-4C10, RCH-ACV, REC-1, Reh, REH, RI-1, RL, RPMI 8226, RPMI-8226, RPMI-8402, RS4-11, "RS4;11", SEM, Set-2, SIG-M5, SK-MM-2, SKM-1, SR, SR-786, ST486, SU-DHL-1, SU-DHL-10, SU-DHL-4, SU-DHL-5, SU-DHL-6, SU-DHL-8, SUP-B15, SUP-B8, SUP-HD1, SUP-M2, SUP-T1, SUP-T11, TALL-1, TF-1, THP-1, TO 175.T, Toledo, TUR, U-266, U-698-M, U-937, U266B1, UT-7, WSU-DLCL2, and WSU-NHL.

In other embodiments, the cancer cell may be in vivo; i.e., the cell may be disposed in a subject. In such embodiments, the cancer cell is contacted with the composition comprising SL or a SL derivative by administering the composition comprising SL or a SL derivative to the subject. A subject may be a rodent, a human, a livestock animal, a companion animal, or a zoological animal. In one embodiment, the subject may be a rodent, e.g. a mouse, a rat, a guinea pig, etc.

In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The cancer cell disposed in the subject may be a blood cancer cell (e.g., leukemia, lymphoma, myeloma, leukemia stem cell). The cancer cell may be a cancer stem cell. The cancer may be primary or metastatic; early stage or late stage; and/or the tumor may be malignant or benign. Non-limiting examples of cancers include acute lymphoblastic leukemia, acute myeloid leukemia, AIDS-related lymphoma, Burkitt lymphoma, central nervous system lymphoma (primary), chronic lymphocytic leukemia, chronic myelogenous leukemia, chronic myeloproliferative disorders, cutaneous T-cell lymphoma, hairy cell leukemia, Hodgkin lymphoma, leukemias (acute lymphoblastic, acute myeloid, chronic lymphocytic, chronic myelogenous, hairy cell), lymphomas (AIDS-related, Burkitt, cutaneous T-cell, Hodgkin, non-Hodgkin, primary central nervous system), Merkel cell carcinoma, multiple myeloma/plasma cell neoplasm, myelodysplastic syndromes, myelodysplastic/myeloproliferative diseases, myelogenous leukemia (chronic), myeloid leukemias (adult acute, childhood acute), multiple myeloma, myeloproliferative disorders (chronic), non-Hodgkin lymphoma, primary central nervous system lymphoma, T-Cell lymphoma (cutaneous), and Waldenström macroglobulinemia. In one exemplary embodiment, the cancer cell may be a leukemia. The leukemia may be an acute lymphocytic (lymphoblastic) leukemia, a chronic lymphocytic leukemia, an acute myeloid leukemia, a chronic myeloid leukemia, a hairy cell leukemia, a T-cell prolymphocytic leukemia, a large granular lymphocytic leukemia, or an adult T-cell leukemia. In a specific embodiment, the cancer is selected from the group consisting of acute myeloid leukemia, chronic myeloid leukemia, chronic lymphocytic leukemia, acute lymphoblastic leukemia, multiple myeloma, myelodisplastic syndrome and myeloproliferative neoplasms.

In certain aspects, a therapeutically effective amount of a composition of the disclosure may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. It is within the skill of one in the art, to determine the route of administration based on the disease or condition to be treated.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the disclosure is administered to a subject. A "therapeutically effective amount" is an amount of the therapeutic composition sufficient to produce a measurable response (e.g., an improvement in symptoms associated with a cancer, a cytotoxic response or tumor regression). Actual dosage levels of active ingredients in a therapeutic composition of the disclosure can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, type of cancer, age, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The timing of administration of the treatment relative to the disease itself and duration of treatment will be determined by the circumstances surrounding the case. Treatment could begin in a hospital or clinic itself, or at a later time after discharge from the hospital or after being seen in an outpatient clinic.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days or every 4 days. In a different embodiment, the frequency of dosing may be one, twice, three or four times monthly. For example, a dose may be administered every 1 week, every 2 weeks, every 3 weeks or every 4 weeks.

Although the foregoing methods appear the most convenient and most appropriate and effective for administration of a composition of the disclosure, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

(b) Inhibiting Cancer Cell Growth

Following contact with an effective amount of the composition comprising SL or a SL derivative, growth of the cancer cell is inhibited. Cell growth or proliferation can be measured in cells grown in vitro using standard cell viability or cell cytotoxicity assays (e.g., based on DNA content, cell permeability, etc.) in combination with cell counting methods (e.g., flow cytometry, optical density). Cell growth or proliferation can be measured in vivo using imaging procedures and/or molecular diagnostic indicators.

In an embodiment, contact with an effective amount of the composition comprising SL or a SL derivative selectively inhibits growth of cancer cells. As such, a composition comprising SL or a SL derivative does not appreciably kill non-cancer cells at the same concentration. Accordingly, more than 50% of non-cancer cells remain viable following contact with a composition comprising SL or a SL derivative at the same concentration. For example about 50%, about 55%, about 60%, about 65%, about 70%, about 75%, about 80%, about 85%, about 90%, about 95% or about 100% of non-cancer cells remain viable following contact with a composition comprising SL or a SL derivative at the same concentration. Or, 50%, 55%, 60%, 65%, 70%, 75%, 80%, 85%, 90%, 95% or 100% of non-cancer cells remain viable following contact with a composition comprising SL or a SL derivative at the same concentration.

Another method to measure selective inhibition of cancer cells may be via determining the LD50 of the SL or SL derivative in the presence of cancer cells. For example, cancer cells may be cultured in the presence of a SL or SL derivative and the LD50 may be calculated via methods standard in the art. A LD50 of a SL or SL derivative of the disclosure may have a LD50 value of about 2 µM or less. For example, a LD50 of a SL or SL derivative of the disclosure may have a LD50 value of about 2 µM or less, about 1.9 µM or less, about 1.8 µM or less, about 1.7 µM or less, about 1.6 µM or less, about 1.5 µM or less, about 1.4 µM or less, about 1.3 µM or less, about 1.2 µM or less, about 1.1 M or less, about 1 µM or less, about 0.9 µM or less, about 0.8 µM or less, about 0.5 µM or less, about 0.4 µM or less, about 0.3 µM or less, about 0.2 µM or less, or about 0.1 µM or less. Further, a LD50 of a SL or SL derivative of the disclosure may have a LD50 value of about 0.1 µM or less. For example, a LD50 of a SL or SL derivative of the disclosure may have a LD50 value of about 0.1 µM or less, about 0.09 µM or less, about 0.08 µM or less, about 0.07 µM or less, about 0.06 µM or less, about 0.05 µM or less, about 0.04 µM or less, about 0.03 µM or less, about 0.02 µM or less, or about 0.01 µM or less.

In various embodiments, cancer cell growth may be inhibited about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. In other embodiments, cancer cell growth may be inhibited to such a degree that the cell undergoes cell death (via apoptosis or necrosis). Any suitable reference value known in the art may be used. For example, a suitable reference value may be cancer cell growth in a sample that has not been contacted with a composition comprising SL or a SL derivative. In another example, a suitable reference value may be the baseline growth rate of the cells as determined by methods known in the art. In another example, a suitable reference value may be a measurement of the number of cancer cells in a reference sample obtained from the same subject. For example, when monitoring the effectiveness of a therapy or efficacy of a composition comprising SL or a SL derivative, a reference sample may be a sample obtained from a subject before therapy or administration of a composition comprising SL or a SL derivative.

In an embodiment, contact with an effective amount a composition comprising SL or a SL derivative inhibits activation of NF-κB. SL or a SL derivative of the disclosure may inhibit activation of NF-κB by interacting with Cys-38 of NF-κB. Inhibition of activation of NF-κB may induce apoptosis. As such, the inhibition of activation of NF-κB may be measured in vitro using standard cell viability or cell cytotoxicity assays in combination with cell counting methods as described above. Or, the inhibition of activation of NF-κB may be measured in vivo using imaging procedures and/or molecular diagnostic indicators. Inhibition of activation of NF-κB may also be measured by measuring nucleic acid expression of NF-κB. Methods to measure nucleic acid expression are known in the art and may include PCR, quantitative PCR, RT-PCR, qRT-PCR, microarray or array.

In various embodiments, expression of NF-κB may be reduced about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. Any suitable reference value known in the art may be used. For example, a suitable reference value may be the expression of NF-κB in a sample that has not been contacted with a composition comprising SL. In another example, a suitable reference value may be the expression of NF-κB in a subject, or group of subjects, of the same species that has no clinically detectable symptom of cancer. In another example, a suitable reference value may be expression of NF-κB in a subject, or group of subjects, of the same species that has no clinically detectable cancer. In another example, a suitable reference value may be the background signal of the assay as determined by methods known in the art. In another example, a suitable reference value may be a measurement of the expression of NF-κB in a reference sample obtained from the same subject. The reference sample may be obtained from a subject when the subject had no clinically detectable symptom of cancer. A skilled artisan will appreciate that it is not always possible or desirable to obtain a reference sample from a subject when the subject is otherwise healthy. For example, when monitoring the effectiveness of a therapy or efficacy of a composition comprising SL, a reference sample may be a sample obtained from a subject before therapy or administration of a composition comprising SL began. In an additional example, a suitable reference sample may be from an individual or group of individuals that has been shown not to have cancer.

(c) Optional Contact

In certain embodiments, the method may further comprise contacting the cell with at least one chemotherapeutic agent and/or a radiotherapeutic agent. The chemotherapeutic agent and/or radiotherapeutic agent may be administered concurrently or sequentially with a composition comprising SL or a SL derivative.

The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lomustine (CCNU), mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur (1-hexylcarbomoyl-5-fluorouracil), cladribine, cytarabine or cytosine arabinoside (Ara-C), dideoxyuridine, denopterin, doxifluridine, enocitabine, floxuridine, fludarabine, 5-fluorouracil, gemcetabine, hydroxyurea, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycins, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, streptonigrin, streptozocin, tubercidin, valrubicin, ubenimex, zinostatin, and zorubicin. Non-limiting examples of suitable anti-cytoskeletal agents include colchicines, docetaxel, macromycin, paclitaxel, vinblastine, vincristine, vindesine, and vinorelbine. Suitable topoisomerase inhibitors include, but are not limited to, amsacrine, etoposide (VP-16), irinotecan, mitoxantrone, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Examples of targeted therapeutic agents include, without limit, monoclonal antibodies such as alemtuzumab, epratuzumab, gemtuzumab, ibritumomab tiuxetan, rituximab, tositumomab, and trastuzumab; protein kinase inhibitors such as bevacizumab, cetuximab, dasatinib, erlotinib, gefitinib, imatinib, lapatinib, mubritinib, nilotinib, panitumumab, pazopanib, sorafenib, sunitinib, and vandetanib; angiogeneisis inhibitors such as angiostatin, endostatin, bevacizumab, genistein, interferon alpha, interleukin-2, interleukin-12, pazopanib, pegaptanib, ranibizumab, rapamycin, thalidomide; and growth inhibitory polypeptides such as erythropoietin, interleukins (e.g., IL-1, IL-2, IL-3, IL-6), leukemia inhibitory factor, interferons, thrombopoietin, TNF-$\alpha$, CD30 ligand, 4-1 BB ligand, and Apo-1 ligand. Also included are pharmaceutically acceptable salts, acids, or derivatives of any of the above listed agents. The mode of administration of the chemotherapeutic agent can and will vary depending upon the agent and the type of cancer. A skilled practitioner will be able to determine the appropriate dose of the chemotherapeutic agent.

The radiotherapeutic agent may include a radioisotope. Suitable radioisotopes include, without limit, Iodine-131, Iodine-125, Iodine-124, Lutecium-177, Phosphorous-132, Rhenium-186, Strontium-89, Yttrium-90, Iridium-192, and Samarium-153. Alternatively, the radiotherapeutic agent may include a high Z-element chosen from gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium. The appropriate dose of the radiotherapeutic agent may be determined by a skilled practitioner.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups:

hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted, or replaced, with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

As various changes could be made in the above compounds, products and methods without departing from the scope of the invention, it is intended that all matter contained in the above description and in the examples given below, shall be interpreted as illustrative and not in a limiting sense.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Use of Hetero-Substituted Cyclic Lactone Analogues as Antileukemic and Cytotoxic Agents In 2015, there have been approximately 20,830 cases of acute myeloid leukemia (AML) and approximately 10,460 deaths due to AML. The median age of patients diagnosed with AML is about 67 years and the overall five-year survival rate is approximately 26%. AML is characterized by a high rate of relapse even after aggressive multi-agent chemotherapy and allogenic stem cell transplantation. This is due in part to the presence of AML stem cells resistant to therapy. Two important characteristics differentiate AML stem cells from normal hematopoetic stem cells: 1. AML stem cells are more sensitive to reactive oxygen species (ROS); and 2. Transcription factor NF-κB is elevated in AML stem cells.

Figure 1B:
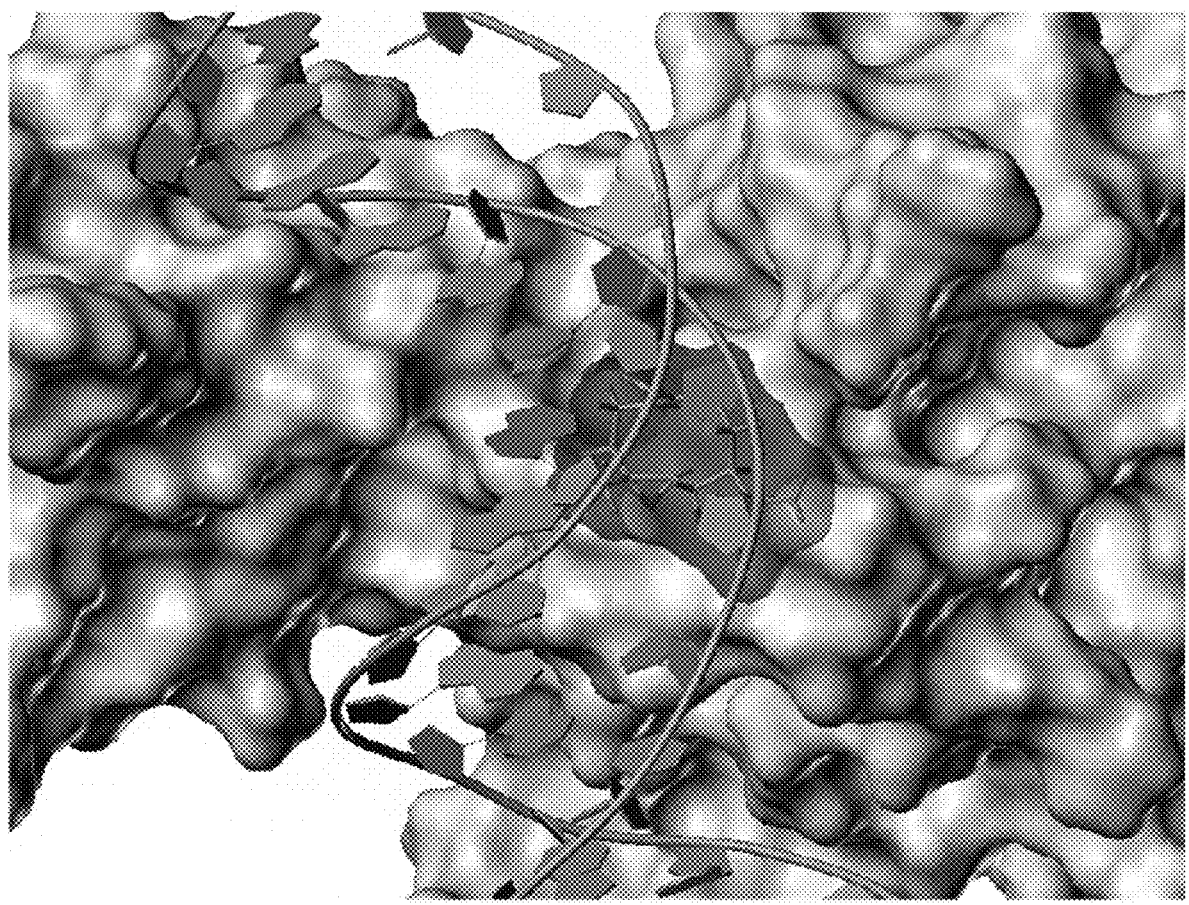
FIG. 1B depicts DHL (in red) binding to NF-κB (gray) thereby preventing binding of DNA (green).
Figure 2A:
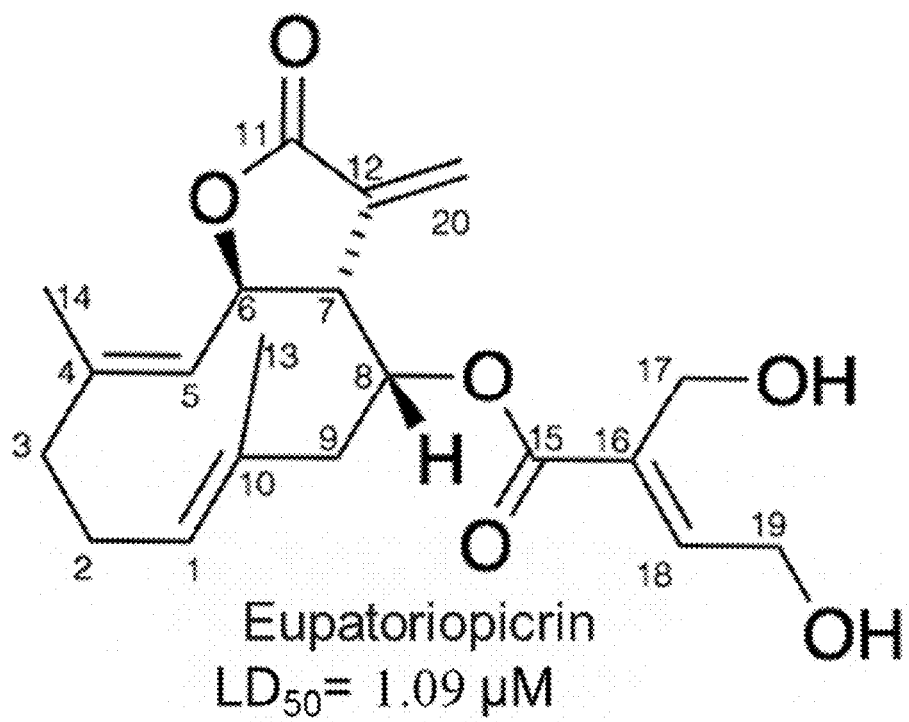
FIG. 2A depicts the structure of Eupatoriopicrin and FIG. 2B depicts the structure of Bahia II. The $LD_{50}$ values indicate their activity against MV4-11 cells.
Figure 2B:
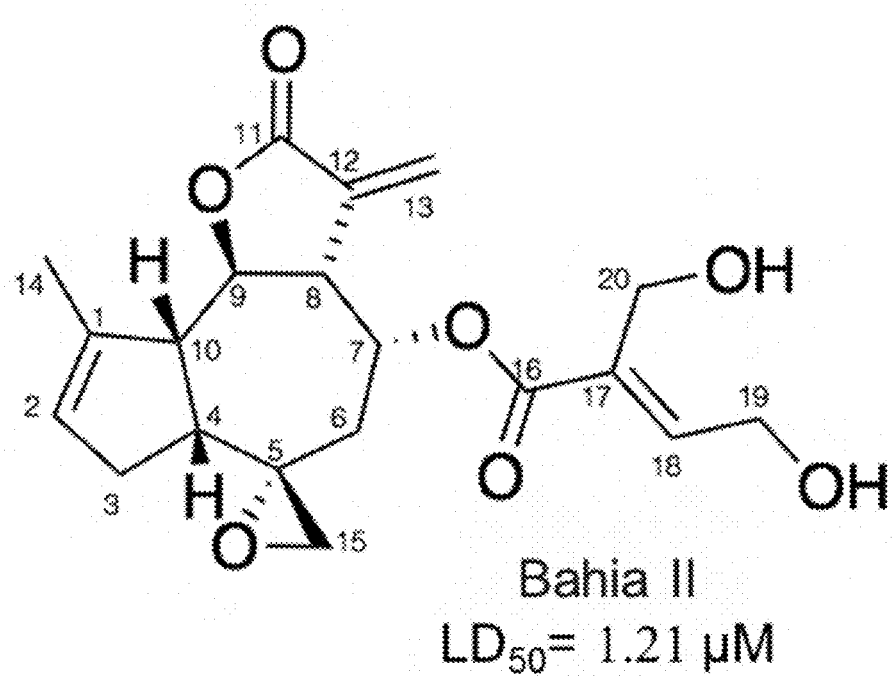
Figure 3A:
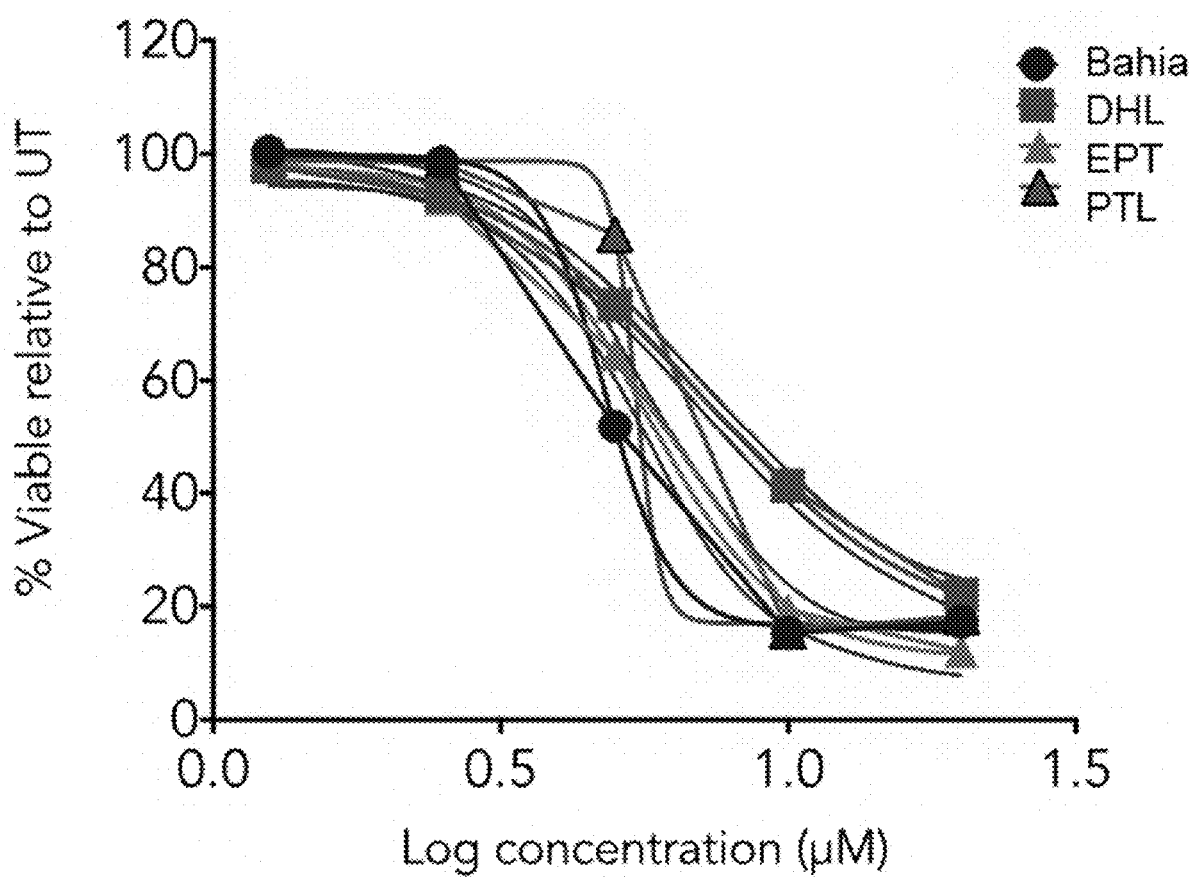
FIG. 3A and FIG. 3B depict graphs showing the activity of Bahia II, Eupatoriopicrin (EPT), DHL and PTL against primary AML samples. $LD_{50}$ of Bahia II is 4.64 µM, $LD_{50}$ of Upatoriopicrin is 5.65 µM, $LD_{50}$ of DHL is 7.06 µM, and $LD_{50}$ of PTL is 5.43 µM.
Figure 3B:
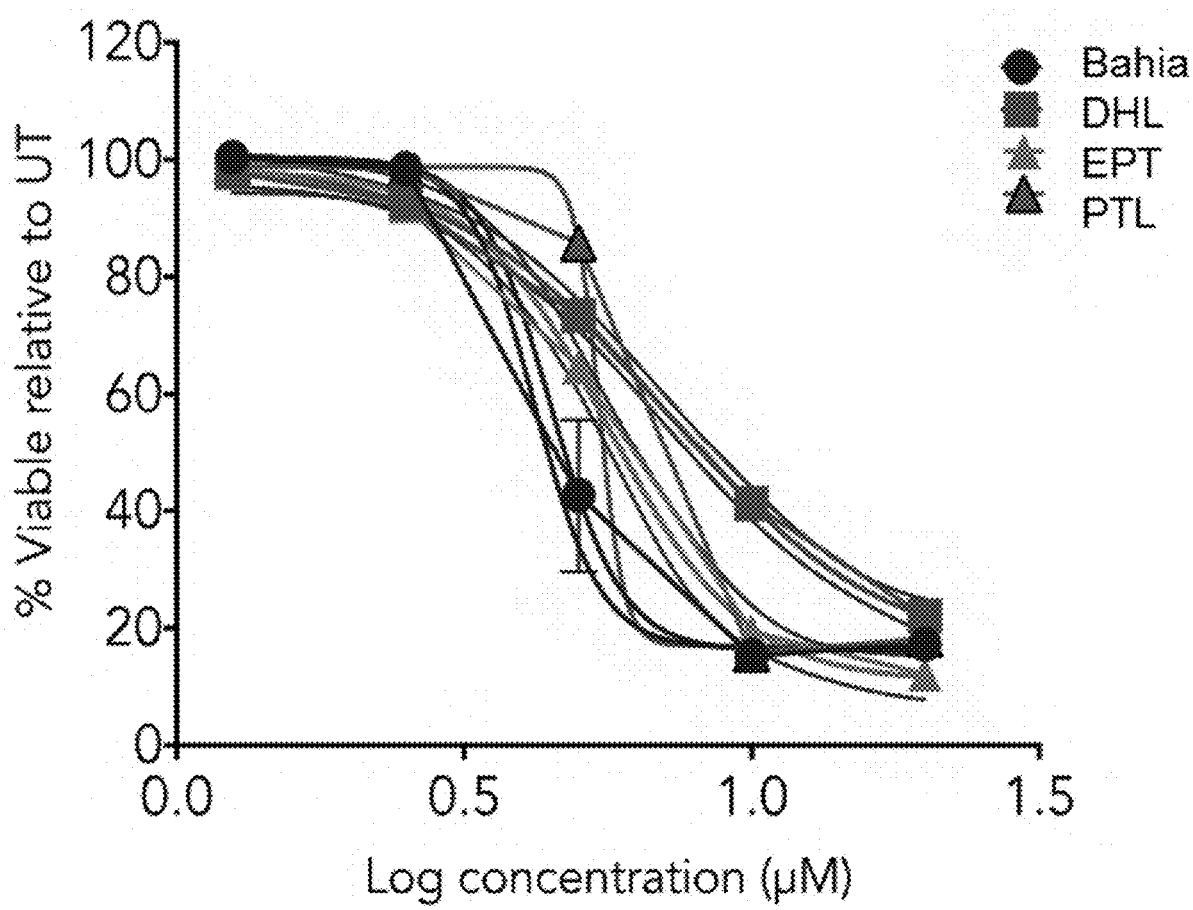

Sesquiterpene lactones (SLs) constitute a large and diverse group of biologically active plant chemicals that have been identified in several plant families. Some sesquiterpene lactones possess anti-inflammatory and/or antitumor activity. For example, parthenolide and a derivative of parthenolide, dehydroleucodine, are highly cytotoxic. SLs react by a nucleophilic addition mechanism with the Cys-38 residue in the p65 subunit of NF-κB thereby preventing it from binding to DNA (FIG. 1). Two SLs, eupatoriopcrin (EPT) (FIG. 2A) and Bahia II (FIG. 2B), have potent activity against MV4-11 cells with $LD_{50}$ values of 1.09 μM and 1.21 μM, respectively. Bahia II and EPT also had potent activity against primary samples of AML comparable to or better than PTL and DHL, respectively (FIG. 3A, FIG. 3B, Table 1). Importantly, Bahia II has outstanding solubility in water (465 μM; 1.75±0.06 mg/ml) as compared to PTL which a solubility of 165 μM (0.409 mg/ml±0.06 mg/ml). This data demonstrates that EPT and Bahia II may be useful anti-AML agents.

TABLE 1

Activity of SLs against AML primary samples.

| Compound | Average $LD_{50}$ (μM) |
|---|---|
| Bahia II | 4.64 |
| Eupatoriopicrin | 5.65 |
| DHL | 7.06 |
| PTL | 5.43 |

Figure 4A:
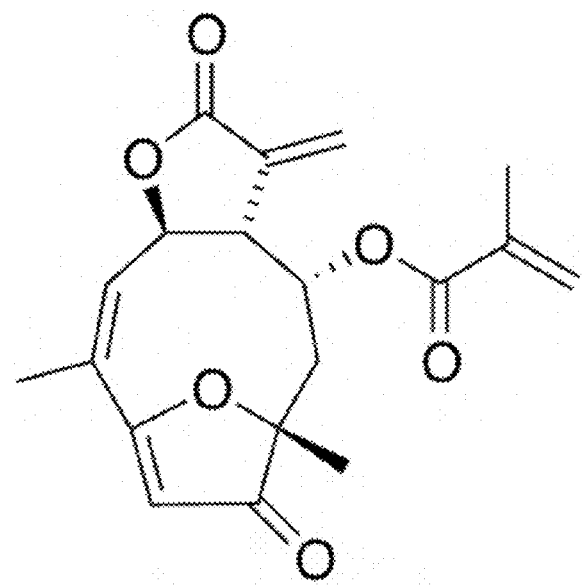
FIG. 4A, FIG. 4B and FIG. 4C depict Group A compounds and their $LD_{50}$ values against MV4-11 cells which include Calaxin (FIG. 4A), PTL (FIG. 4B) and DHL (FIG. 4C).
Figure 5A:
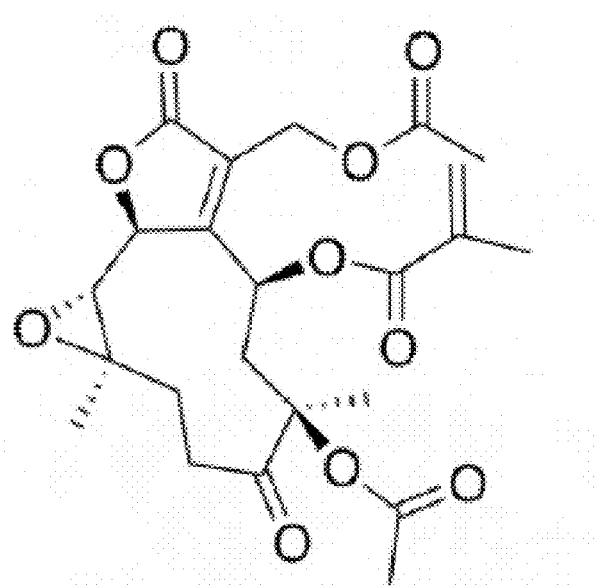
FIG. 5A and FIG. 5B depict Group B compounds and their $LD_{50}$ values against MV4-11 cells which include Glaucolide A (FIG. 5A) and Glaucolide E (FIG. 5B). The Group B compounds have an alternative site for nucleophilic attack in the methacrylate ester side chain.
Figure 11:
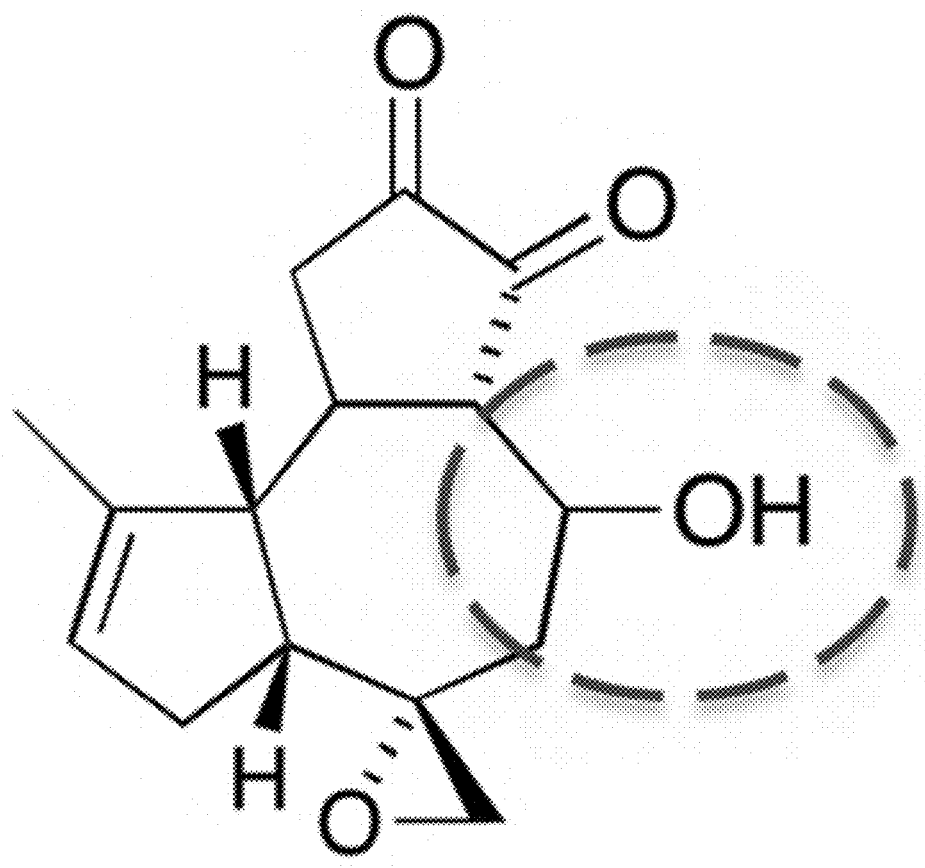
FIG. 11 depicts the structure of Bahia I.

Following this promising data, additional SLs were studied. This included glaucolide A (FIG. 5A), glaucolide E (FIG. 5B) and calaxin (FIG. 4A). Further, an additional compound Bahia I (FIG. 11) was synthesized (described below) and evaluated. The cytotoxicity of these compounds was determined using the AML cell line, MV4-11. MV4-11 cells were treated with the compounds at varying concentrations in triplicate. Cells were then stained with YO-PRO-1 and 7-aminoactinomycin D (7-AAD). YO-PRO-1 stains apoptotic cells and 7-ADD detects cell permeability. At 36 hours cell viability was measured via flow cytometry. Table 2 shows the experimental results. The new SLs were more potent than DHL against MV4-11 cells. The activity of Bahia I demonstrates that a polar substitution adjacent to the lactone ring maintains activity of the compound. The polar substitution in place of the methacrylate side chain but still demonstrating activity allows the development of compounds that have increased water solubility.

TABLE 2

Cytotoxic activity of SLs against MV4-11 cells.

| SLs | $LD_{50}$ (μM) | Type of SLs |
|---|---|---|
| Calaxin | 0.0544 | germacranolide |
| Eupatoriopicrin | 1.09 | germacranolide |
| Glaucolide E | 1.12 | germacranolide |
| Bahia II | 1.21 | guaianolide |
| Glaucolide A | 1.82 | germacranolide |
| Parthenolide | 2.39 | germacranolide |
| Dehydroleucodine | 3.19 | guaianolide |
| Bahia I | 2.80 | guaianolide |

Figure 4B:
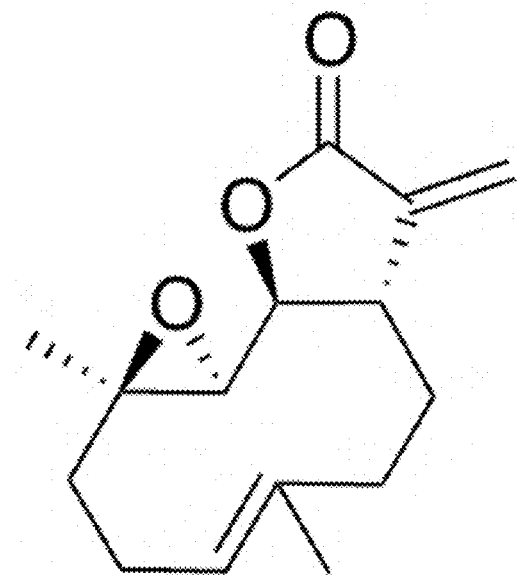
Figure 4C:
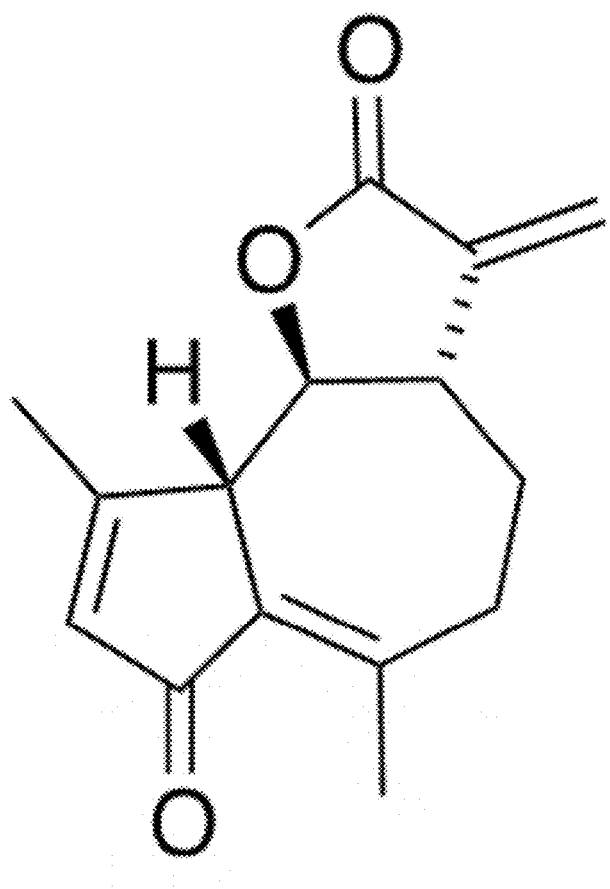
Figure 5B:
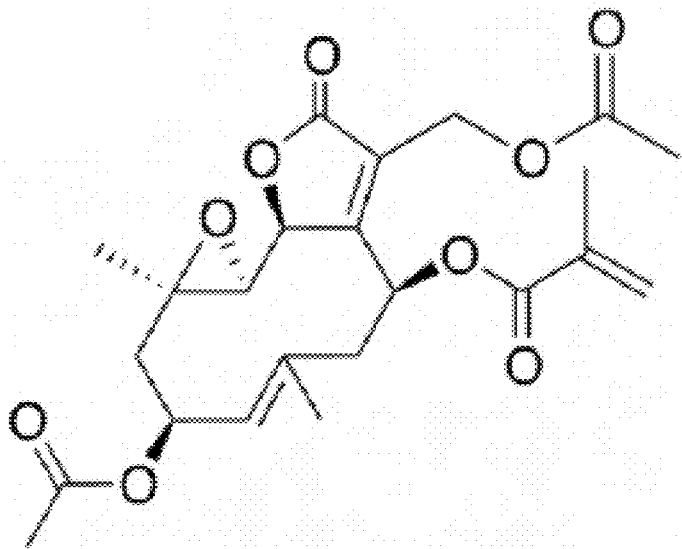

The SLs were classified into two groups, Group A and Group B, based on their reactive groups. Group A compounds included calaxin (FIG. 4A), eupatoriopicrin (FIG. 2A), Bahia II (FIG. 2B), PTL (FIG. 4B) and DHL (FIG. 4C). Group B compounds, which include an alternative site for nucleophilic attack in the methacrylate ester side chain, included glaucolide A (FIG. 5A) and glaucolide E (FIG. 5B).

Figure 6:
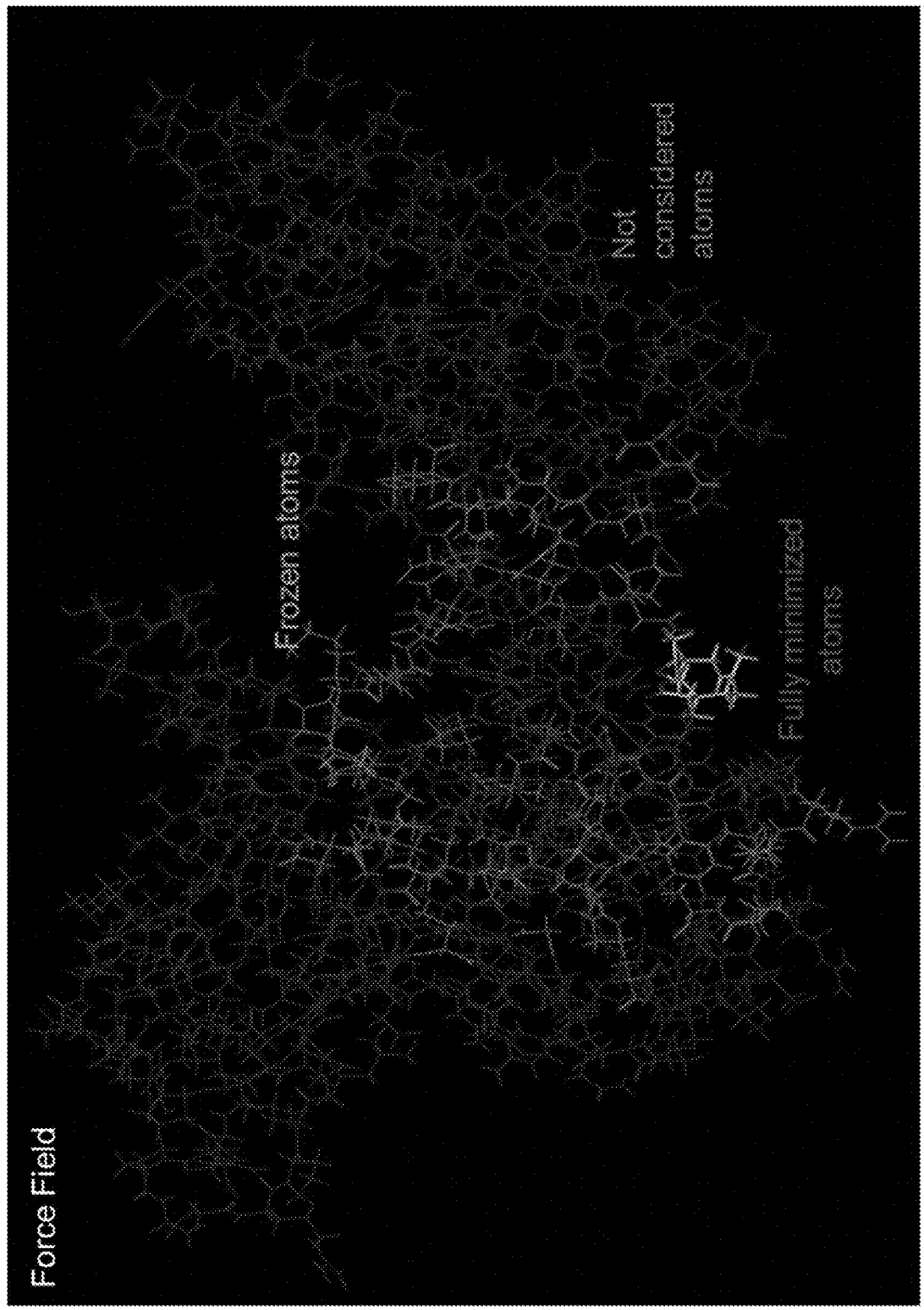
FIG. 6 depicts a stick diagram of a SL bound to NF-κB.
Figure 7:
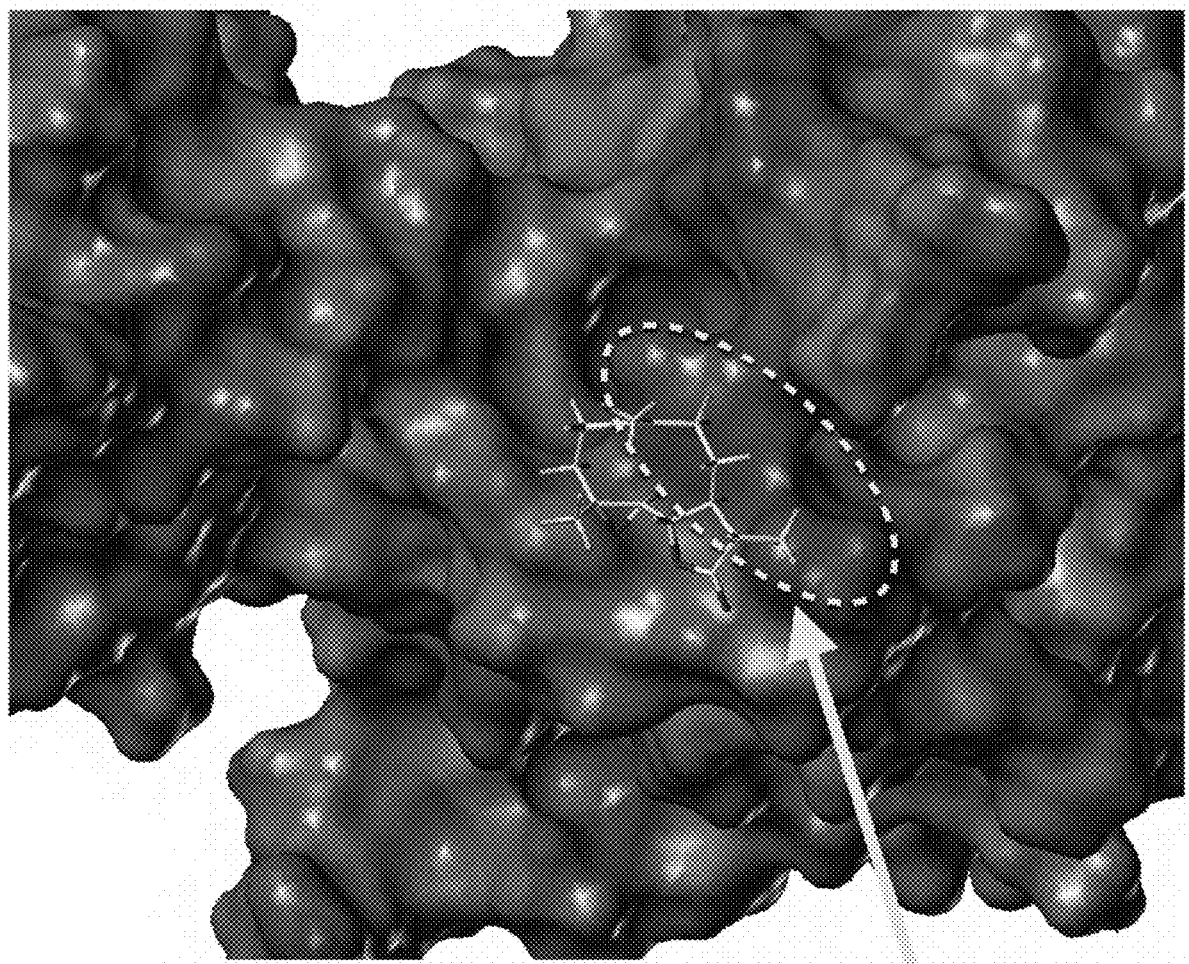
FIG. 7 depicts the lipophilic surface of NF-κB (green) interacting with PTL. The area encircled in yellow corresponds to Tyr-36 and Cys-38 of NF-κB.
Figure 8:
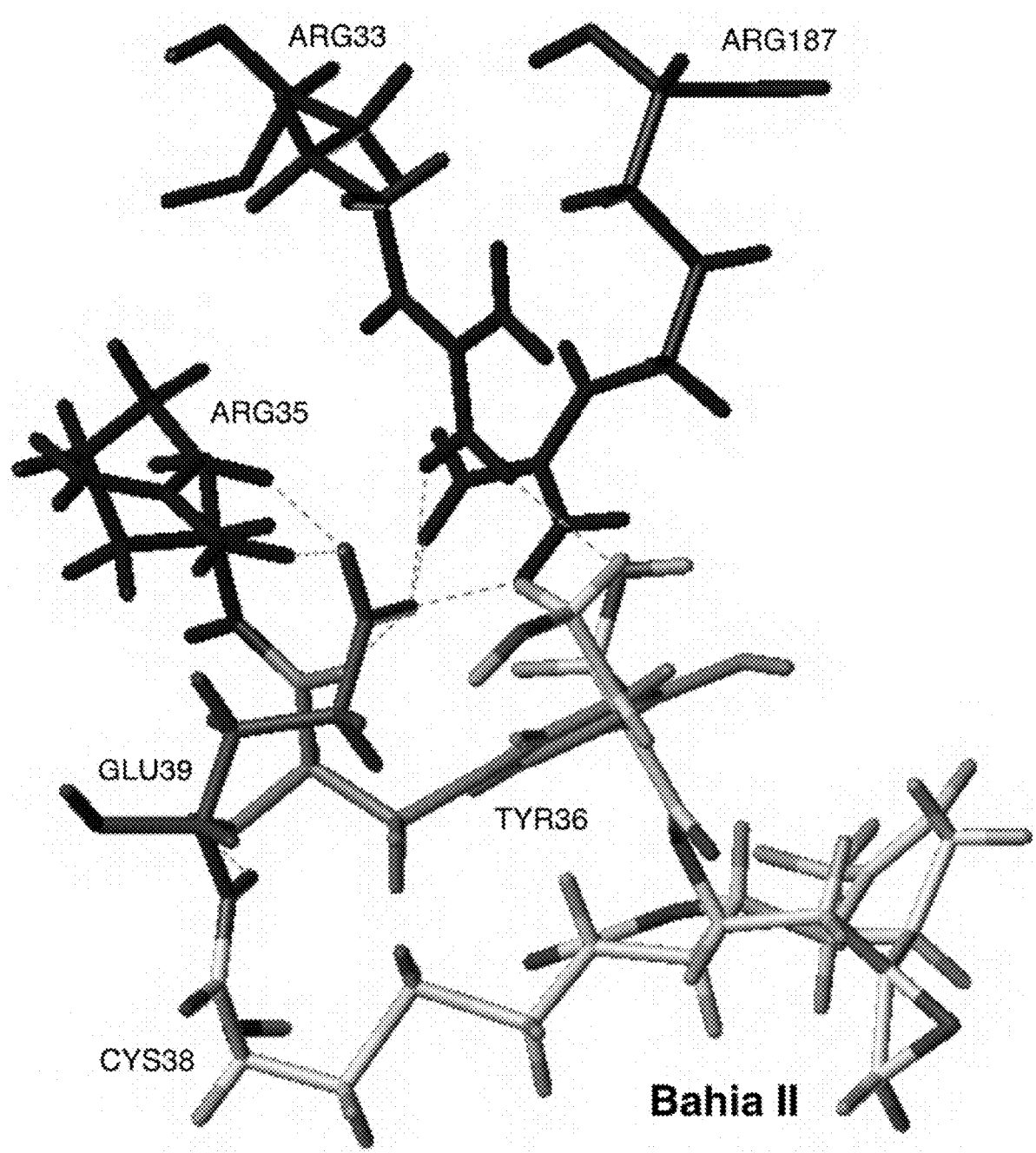
FIG. 8 depicts the binding of Bahia II to NF-κB. Tyr-36 and Cys-38 of NF-κB are interacting with Bahia II.
Figure 9:
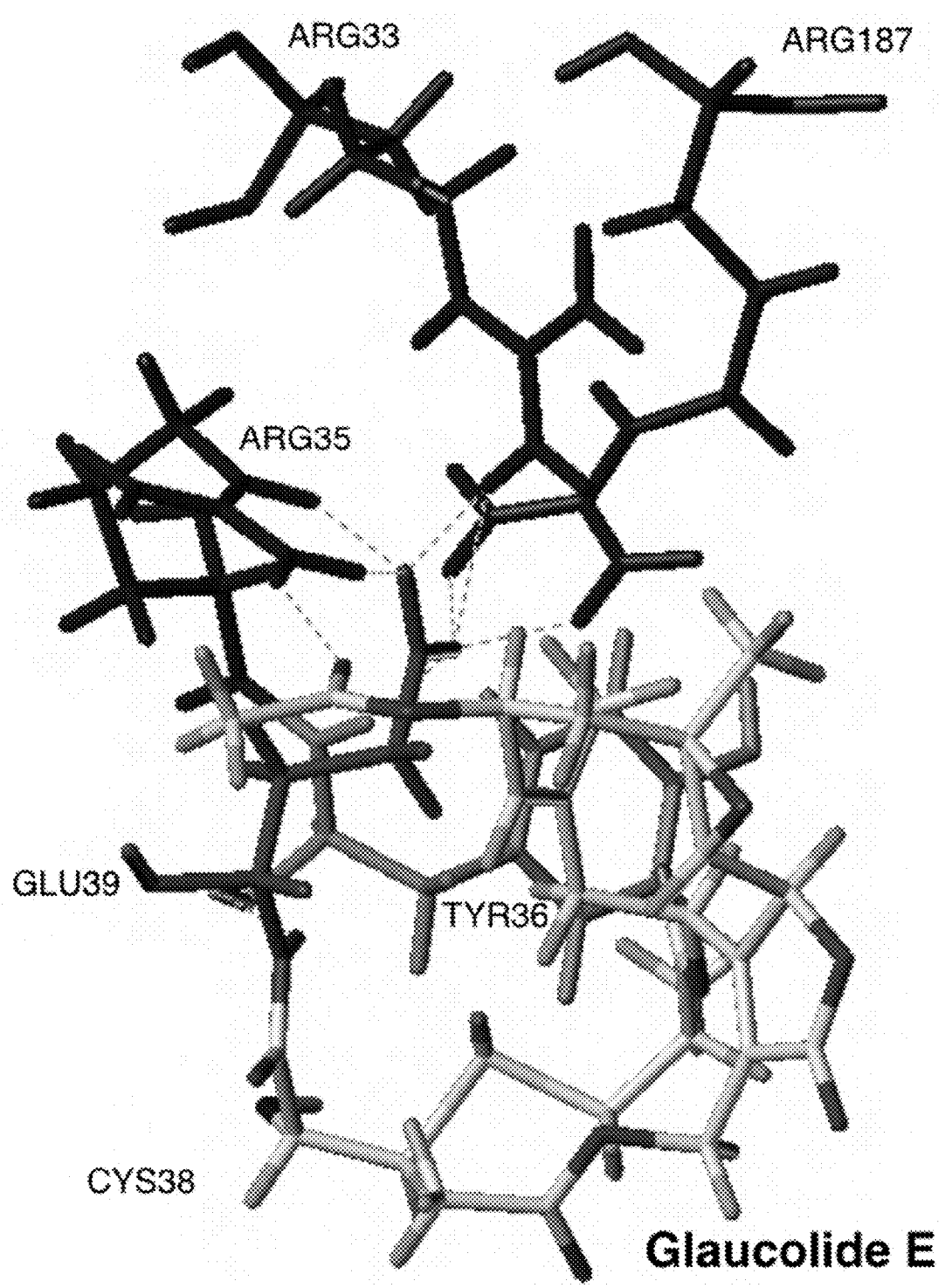
FIG. 9 depicts the binding of Glaucolide E to NF-κB. Glaucolide E forms a feasible adduct with Cys-38 that is stabilized by forming hydrogen bonds with Arg-35 in addition to hydrophobic interactions of Tyr-36 with the methyl group in the methacrylate ester side chain.
Figure 10:
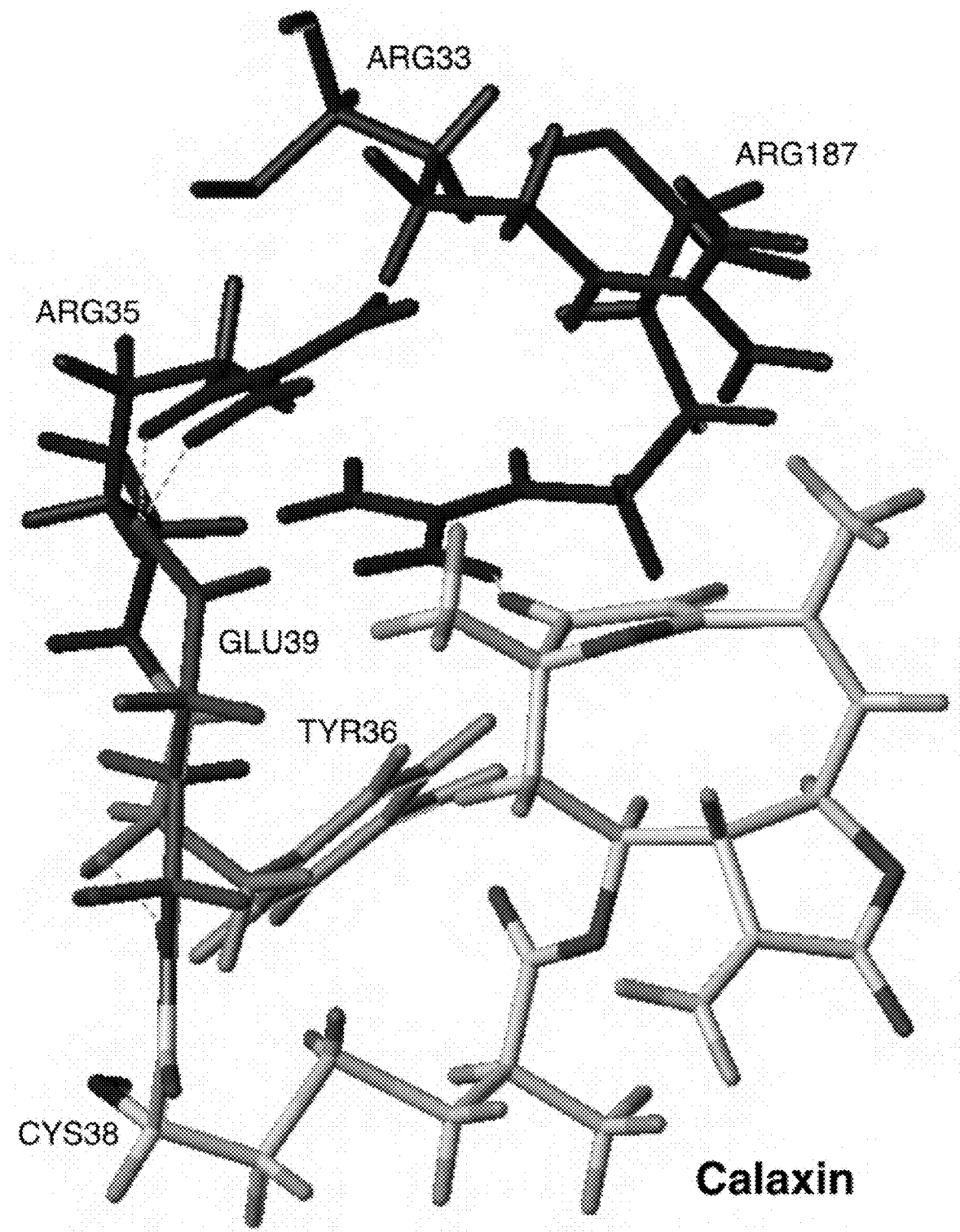
FIG. 10 depicts the binding of Calaxin to NF-κB. Calaxin has both the Group A surface signature and the Group B ability to form a covalent bond with NF-κB via the methacrylate ester. The two active sites in this molecule seems to produce a very substantial increase in its potency.

To understand the characteristics of the SLs, surface signature analysis was performed. The program SYBYLX 2.1.1 was used and the structures of all the compounds were obtained from X-ray crystal analysis. Atomic charges were obtained with the quantum mechanics semi-empirical method PM3 implemented in MOPAC 6.0. Molecular modeling of the binding of SLs to NF-κB was evaluated. The X-ray crystal structure of NF-κB was retrieved from the Protein Data Bank. Then, DNA was extracted from the active site of NF-κB and the NF-κB protein was minimized using the Powell method to relieve conformational strains (FIG. 6). The analysis revealed that the lipophilic surface of NF-κB, corresponding to Tyr-36 and Cys-38, interacted with the lipophilic surface of the SL (FIG. 7). FIG. 8 demonstrates binding of Bahia II to NF-κB. Cys-38 and Tyr-36 are show interacting with Bahia II. The binding of Group B compounds to NF-κB was then evaluated. Binding of glaucolide E to NF-κB showed that gluacolide E form as feasible adduct with Cys-38 that is stabilized by forming hydrogen bonds with Arg-35 in addition to hydrophobic interactions of Tyr-36 with the methyl group in the methacrylate ester side chain (FIG. 9). The binding of to NF-κB was then evaluated. Calaxin, the most active compound, has the ability to form a covalent bond between the methacrylate ester and NF-κB, as well directly with the exocyclic double bond of the lactone ring. It appears that the two active sites in this molecule seem to produce a very substantial increase in its potency (FIG. 10).

Example 2. Preparation of Bahia I

Figure 12:
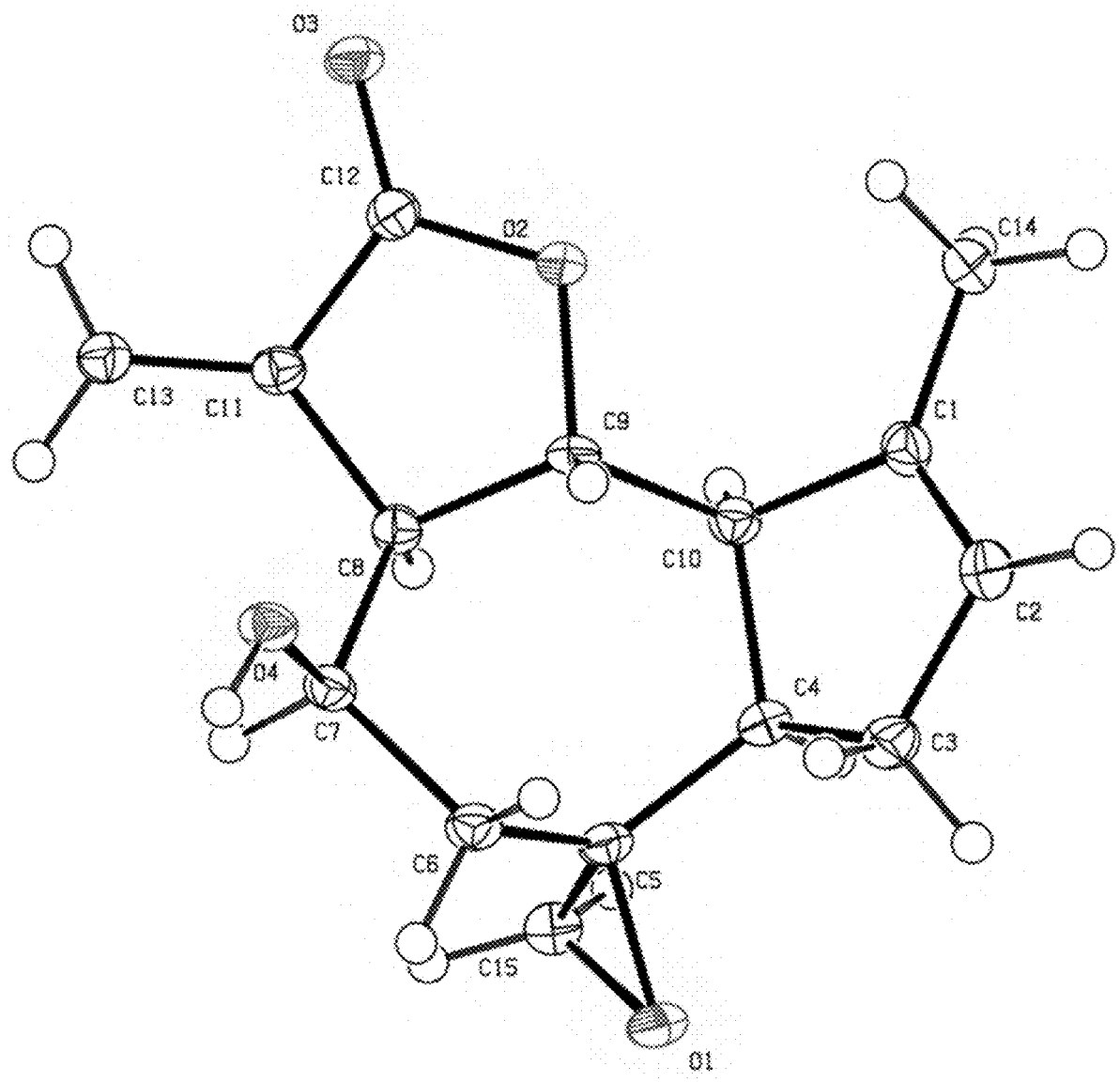
FIG. 12 depicts the 3-D-ORTEP projection of the X-ray crystal structure of Bahia I with 50% probability ellipsoids.

A mixture of bahia II (2) (0.13 mmol), 1 mL of methanol and 10 mL of aqueous LiOH (1.3 mmol) was stirred at room temperature for an hour. The pH of the reaction mixture was adjusted to 5 using acetic acid and then was extracted with ethyl acetate. The organic layer was dried using anhydrous sodium carbonate, evaporated under reduced pressure and the residue was further purified by column chromatography (silica gel, ethyl acetate). The compound was crystallized using acetone-isopropyl ether yielding 25 mg (70%) of compound 3. The synthesis of the bahia I (3), carried out following Scheme 1. Bahia I was isolated as colorless crystals (EtOAc) of mp 190-191° C. The UV spectrum in MeOH exhibited a maximum at λ (log e) 208 (3.33) nm. The IR (ATR) spectrum shows a broad band at 1750 cm$^{-1}$ corresponding to the γ-lactone group, and an exocyclic methylene group 1650 cm$^{-1}$. The EI spectrum showed the molecular ion at m/z 262.2 with low intensity 4.44% with other fragments at m/z (rel. int. %) 91.10 (100), 69.20 (66.13), 232.20 (36.92). Bahia I was further characterized by their $^1$H and $^{13}$C NMR chemical the proton and carbon resonances from C1 to C15 appeared with almost the same chemical shifts and similar multiplicities as in bahia II. Crystallization from ethyl acetate yielded colorless crystals of 3. Crystal data: $C_{15}H_{18}O_4$, mw=262.29, space group P21 21 21, a=7.5935 (2) Å, b=12.1284 (3) Å, c=13.6528 (3) Å, V=1257.38 (5) Å$^3$, Z=4, T=90 K, $D_c$=1.386 g/cm$^3$, $R_1$=0.0272 (w$R_2$=0.0704) (FIG. 12). Deposition number: CCDC 1424442.

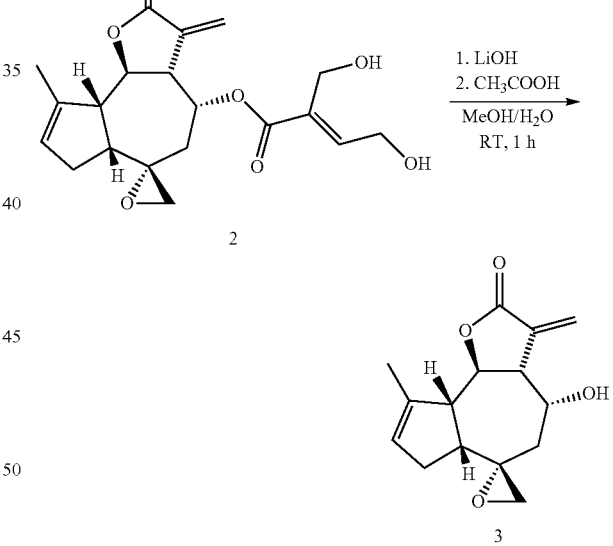

Scheme 1

Example 3. In Vivo Evaluation of SL Compounds

Figure 13A:
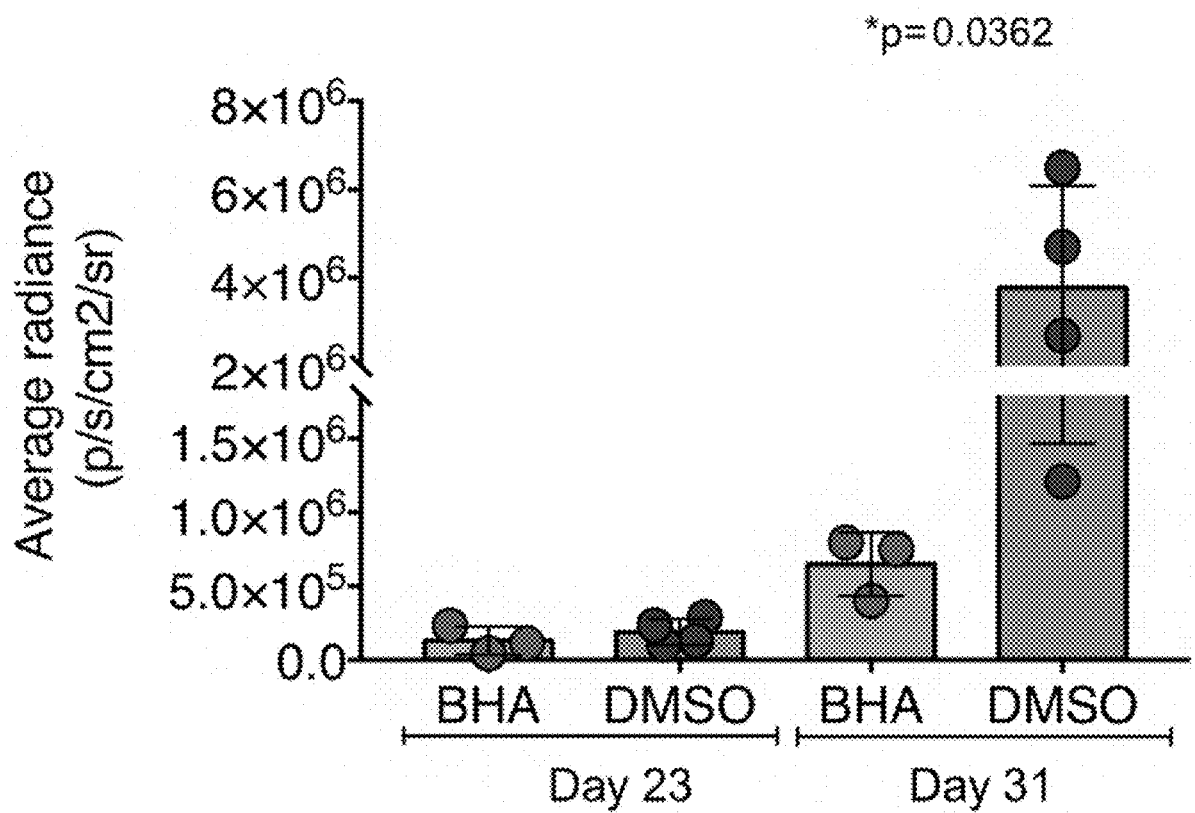
FIG. 13A and FIG. 13B depict the in vivo activity of Bahia II.
Figure 13B:

To evaluate the efficacy of bahia II (BAH) in vivo, 6-8 week old NSG mice were injected i.v. via tail vein with 2.5×10$^5$ MOLM-13_BLIV cells. Two weeks after injection mice were injected with 3 mg of luciferin to visualize the leukemia cells using the IVIS Spectrum Imager. This was denoted time 0. Mice were randomized into 2 groups: (1) Vehicle (DMSO 20%) and (2) bahia II (BAH) (2.5 mg/kg in 20% DMSO). Mice were treated with vehicle or BAH every other day. After 3 doses, administered by i.p. injection, mice were imaged to evaluate tumor progression (Day 23). One week after the first 3 doses, the mice were treated and evaluated again in the same manner (Day 31). FIG. 13A and FIG. 13B show that there was a significant reduction in radiance in the presence of BAH. Accordingly, BAH significantly reduces tumor cells in vivo.

Figure 14:
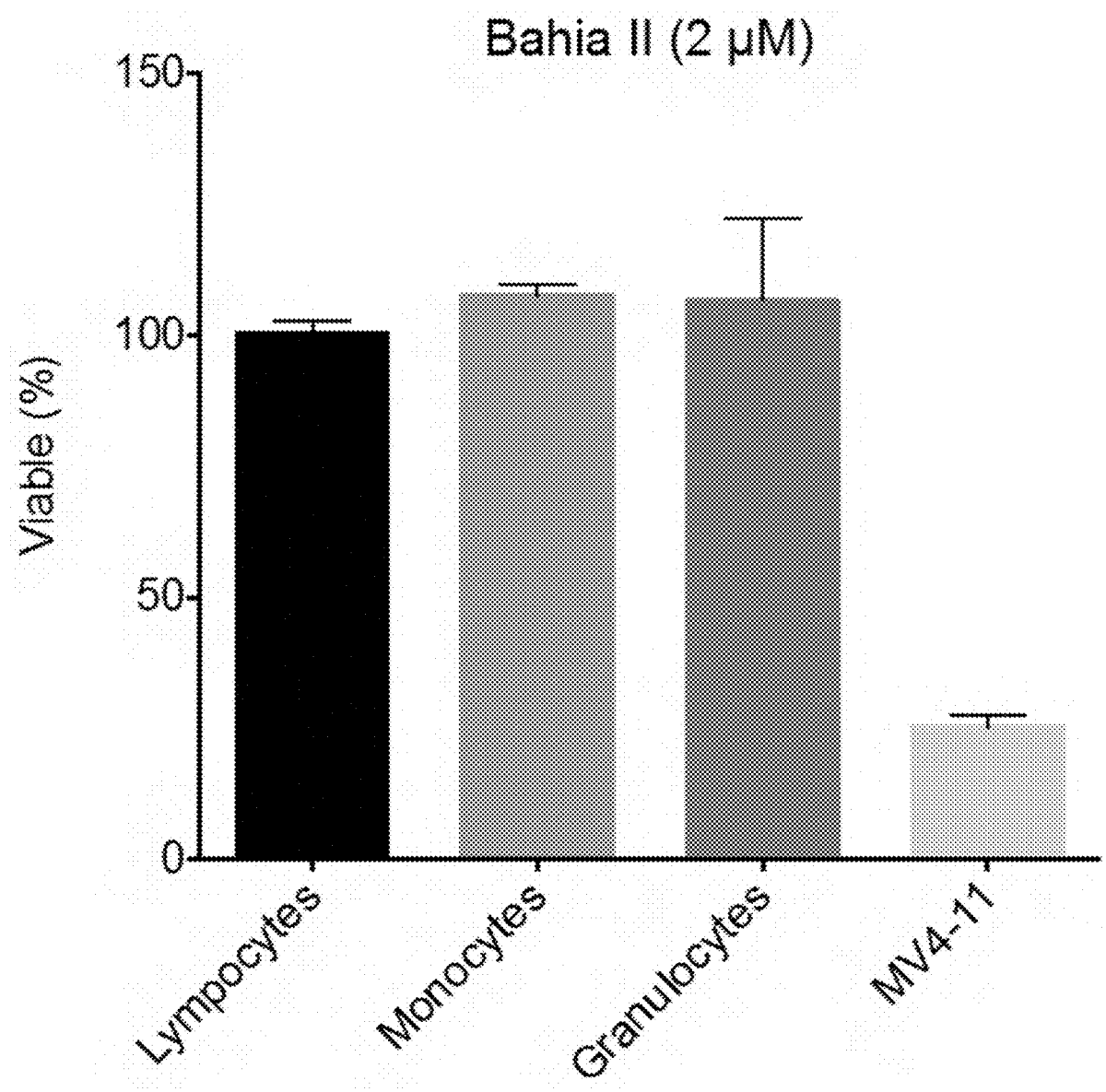
FIG. 14 depicts the comparison of the toxicity of Bahia II against normal peripheral blood mononuclear cells (PBMNCs) and leukemic cells

The cytotoxicity of Bahia II against leukemic cells was compared with its activity against normal peripheral blood mononuclear cells (PBMNCs) (FIG. 14). The results of this experiment show that Bahia II is has much lower toxicity against normal cells that against leukemia cells.

What is claimed is:

1. A method for inhibiting growth of a cancer cell derived from a blood cancer, the method comprising contacting the cancer cell with an effective amount of a composition comprising a compound of Formula (II) or a pharmaceutically acceptable salt thereof:

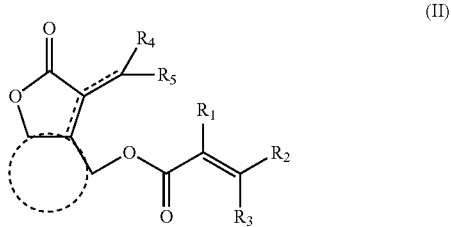

(II)

wherein:
$R_1$, $R_2$ and $R_3$ are independently selected from the group consisting of hydrogen, hydrocarbyl and substituted hydrocarbyl, wherein one or more of $R_1$, $R_2$ and $R_3$ comprise a substituted hydrocarbyl comprising an atom selected from the group consisting of fluorine, oxygen, nitrogen, chlorine, bromine, and iodine;
$R_4$ and $R_5$ are independently selected from the group consisting of hydrogen, hydrocarbyl and substituted hydrocarbyl;

------ is a single or double bond; and

⃝ is a SL ring structure, minus the lactone ring, from the class of guaianolides.

2. The method of claim 1, wherein $R_4$ and $R_5$ are independently selected from the group consisting of hydrogen, —OCOCH$_3$, alkoxy, hydroxyalkyl, carbonylalkyl, carbonyl substituted alkyl, carbonylalkoxy, carbonylaminoalkyl, alkyl, substituted alkyl, ester, substituted ester, alkenyl, substituted alkenyl, alkynyl and substituted alkynyl.

3. The method of claim 1, wherein the lactone ring does not contain a double bond, comprises an α-methylene group and $R_4$ and $R_5$ are hydrogen.

4. The method of claim 1, wherein the lactone ring contains a double bond, does not comprise an α-methylene group, $R_4$ is hydrogen and $R_5$ is selected from the group consisting of —OCOCH$_3$, alkyl, substituted alkyl, ester and substituted ester.

5. The method of claim 1, wherein the lactone ring contains a double bond, does not comprise an α-methylene group, $R_4$ is hydrogen and $R_5$ is OCOCH$_3$.

6. The method of claim 1, wherein the compound of Formula (II) is bahia II.

7. The method of claim 1, wherein the compound of Formula (II) has an LD$_{50}$ in vitro of 2 μM or less.

8. The method of claim 1, wherein the cancer cell is a leukemic cell.

9. The method of claim 1, wherein the cancer cell is a cancer stem cell.

10. The method of claim 1, wherein the cancer cell is in vivo or in vitro.

11. The method of claim 1, wherein the compound of Formula (II) interacts with Cys-38 of NF-κB.

12. The method of claim 1, wherein the inhibiting growth is measured as the expression of NF-κB.

13. The method of claim 1, wherein the blood cancer is selected from the group consisting of acute myeloid leukemia, chronic myeloid leukemia, chronic lymphocytic leukemia, acute lymphoblastic leukemia, multiple myeloma, myelodisplastc syndrome and myeloproliferative neoplasms.

* * * * *